(12) United States Patent
Gao et al.

(10) Patent No.: US 6,191,160 B1
(45) Date of Patent: Feb. 20, 2001

(54) SPIRO-INDOLINES AS Y5 RECEPTOR ANTAGONISTS

(75) Inventors: Ying-Duo Gao, Edison; Douglas J. MacNeil, Westfield; Lihu Yang, Edison; Nancy R. Morin, Cranford, all of NJ (US); Takehiro Fukami, Ibaraki (JP); Akio Kanatani, Ibaraki (JP); Takahiro Fukuroda, Ibaraki (JP); Yasuyuki Ishii, Saitama (JP); Masaki Ihara, Ibaraki (JP)

(73) Assignees: Merck & Co., Inc., Rahway, NJ (US); Banyu Pharmaceutical Co., Ltd., Tokyo (JP)

( * ) Notice: Under 35 U.S.C. 154(b), the term of this patent shall be extended for 0 days.

(21) Appl. No.: 09/436,120

(22) Filed: Nov. 8, 1999

Related U.S. Application Data

(60) Provisional application No. 60/107,835, filed on Nov. 10, 1998.

(51) Int. Cl.[7] ............... A61K 31/495; A61K 31/40; C07D 239/02; C07D 209/54; C07D 277/60
(52) U.S. Cl. ............ 514/409; 514/255.05; 514/275; 514/278; 514/361; 514/371; 514/397; 514/407; 514/409; 544/330; 544/407; 546/15; 548/128; 548/147; 548/301.1; 548/357.5; 548/408
(58) Field of Search ............... 548/128, 147, 548/301.1, 357.5, 408; 514/255.05, 275, 278, 361, 371, 397, 407, 409; 544/330, 407; 546/15

(56) References Cited

U.S. PATENT DOCUMENTS

| | | |
|---|---|---|
| 5,602,024 | 2/1997 | Gerald et al. ............... 435/325 |
| 5,919,901 | 7/1999 | Hu et al. .................... 530/350 |
| 5,939,362 | 8/1999 | Johnson et al. .............. 507/939 |
| 5,968,819 | 10/1999 | Gerald et al. ............... 435/325 |
| 5,989,834 | 11/1999 | Gerald et al. ............... 435/7.2 |
| 5,989,920 | 11/1999 | Gerald et al. ............... 436/50 |

FOREIGN PATENT DOCUMENTS

| | | |
|---|---|---|
| 198 24 175 A1 | 12/1999 | (DE) . |
| 945 438 A1 | 9/1999 | (EP) . |
| 945 439 A1 | 9/1999 | (EP) . |
| 945 440 A1 | 9/1999 | (EP) . |
| 955 293 A1 | 11/1999 | (EP) . |
| WO 96/16542 | 6/1996 | (WO) . |
| WO 97/19682 | 6/1997 | (WO) . |
| WO 97/20820 | 6/1997 | (WO) . |
| WO 97/20822 | 6/1997 | (WO) . |
| WO 97/20823 | 6/1997 | (WO) . |
| WO 97/37998 | 10/1997 | (WO) . |
| WO 97//46250 | 12/1997 | (WO) . |
| WO 98/47505 | 10/1998 | (WO) . |
| WO 98/52890 | 11/1998 | (WO) . |
| WO 99/32466 | 7/1999 | (WO) . |
| WO 99/48873 | 9/1999 | (WO) . |
| WO 99/48888 | 9/1999 | (WO) . |
| WO 99/55667 | 11/1999 | (WO) . |

OTHER PUBLICATIONS

Gerald, et al., "A Receptor Subtype involved in Neuropeptide–Y–. . . ", Nature, vol. 382, pp. 168–171, Jul. 11, (1996).
Hu, et al., "Identification of a Novel Hypothalamic Neuropeptide . . . ", J. ofBiological Chem., vol. 271, No. 42, pp. 26315–26319, Oct. 18, (1996).
Nakamura, et al., "Molecular cloning, organization and . . . ", Biochimica et Biophysica Acta 1328 pp. 83–89, (1997).
Schaffhauser, et al., "Inhibition of Food Intake by Neuropeptide Y Y5 . . . ", Diabetes, vol. 46, pp. 1792–1798, Nov. (1997).
Marsh, et al., "Role of the Y5 neuropeptide Y Receptor . . . ", Nature Medicine, vol. 4, pp. 718–721, Jun. (1998).
Widdowson, P.S., "Regionally–selective down–regulation of NPY Y5 . . . ", Brain Research, 758, pp. 17–25, (1997).
Xin, et al., "Down–Regulated NPY receptor subtype–5 mRNA . . . ", NeuroReport 9, pp. 737–741, (1998).
Bobowski, 3,4,9,9a Tetrahydro–1,4–ethano–3, 4a(iminoethano)–4aH–carbozol–2(1H)one Derivatives. (J. Org. Chem., 50(7), pp. 929–931), 1985.*
Bobowski, et al., 3,4,9,9a Tetrahydro–1,4–ethano–3, 4a(iminoethano)–4aH–carbazol–2(1H)–one Derivatives and N,3–Disubstituted 3,3a,4,4a,10, 10a–Hexahydro–3a–hydroxy–2oxo–1,9b:4, 10–dietanoimidazol[4,5–b]carbazole–5(2H)–carboxamide (J. Org. Chem., 46(24), pp. 4927–4931), 1981.*

* cited by examiner

Primary Examiner—Mukund J. Shah
Assistant Examiner—Ben Schroeder
(74) Attorney, Agent, or Firm—Nicole M. Wallinger; Melvin Winokur

(57) ABSTRACT

Compounds of the general structural formula I

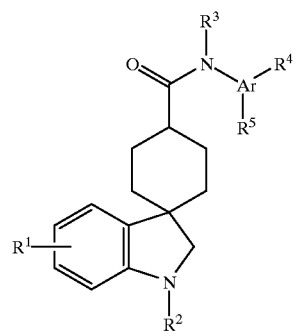

are selective NPY Y5 receptor antagonists. The compounds and compositions of the present invention are useful in the treatment of obesity and complications associated therewith.

15 Claims, No Drawings

SPIRO-INDOLINES AS Y5 RECEPTOR ANTAGONISTS

This application claims the benefit of U.S. Provisional Application Ser. No. 60/107,835, filed Nov. 10, 1998.

SUMMARY OF THE INVENTION

This invention is concerned with compounds which are spiro-indolines of general structure:

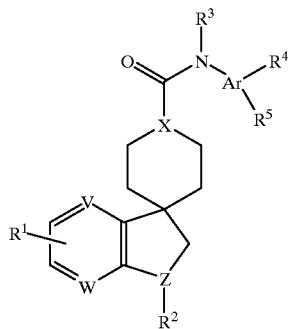

The invention is also concerned with the use of these novel compounds to selectively antagonize the Y5 receptors and thereby inhibit obsessive food intake and the resulting obesity and complications associated therewith.

The invention is also concerned with pharmaceutical formulations comprising one of the compounds as active ingredient.

The invention is further concerned with processes for preparing the compounds of this invention.

BACKGROUND OF THE INVENTION

Neuropeptide Y (NPY) is a member of the pancreatic polypeptide family with widespread distribution throughout the mammalian nervous system. NPY and its relatives elicit a broad range of physiological effects through activation of at least six G protein-coupled receptor subtypes known as Y1, Y2, Y3, Y4, Y5 and Y6. The Y5 subtype was isolated, characterized and reported recently in U.S. Pat. No. 5,602,024 (WO 96/16542).

The cited WO 96/16542 also reports the discovery of chemical compounds which bind selectively to the Y5 receptor and which act as antagonists of the Y5 receptor, several of which were shown to inhibit food intake in rats.

Now with the present invention there is provided a class of compounds characterized as spiro-indolines, which are useful in the treatment, control or prevention of diseases, disorders or conditions mediated by activation of the Y5 receptor. These compounds are, thus, useful in the treatment of obesity in man or animals and in conditions caused by or exacerbated by obesity.

DETAILED DESCRIPTION OF THE INVENTION

The compounds of this invention are represented by the compound of structural formula I:

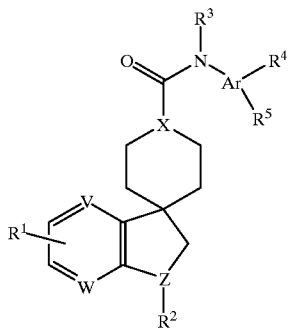

or a pharmaceutically acceptable salt thereof, wherein;

V, W, X and Z are independently selected from CH and N;

$R^1$ is H, $C_{1-3}$ alkyl, $C_{1-3}$ alkoxy, F, or Cl;

$R^2$ is $S(O)_nR^6$, $COR^6$ or CHO, wherein
n is 0, 1 or 2; and
$R^6$ is $N(R^3)_2$ or $C_{1-3}$ alkyl;

$R^3$ is independently H or $C_{1-3}$ alkyl;

Ar is aryl or heteroaryl;

$R^4$ and $R^5$ are independently selected from:
(1) hydrogen,
(2) aryl, either unsubstituted or substituted with
    (a) halo
    (b) $C_{1-3}$ alkoxy,
    (c) —$N(C_{1-3}$ alkyl$)_2$,
    (d) $C_{2-4}$ alkanoyl, or
    (e) aryl,
(3) nitro,
(4) $C_{1-5}$ alkyl,
(5) $C_{1-5}$ alkoxy,
(6) hydroxy-$C_{1-3}$ alkyl,
(7) carboxy,
(8) halo,
(9) $C_{1-5}$ alkylthio,
(10) $C_{1-5}$ alkoxycarbonyl,
(11) pyridylcarbonyl,
(12) benzoyl,
(13) phenyl-$C_{1-3}$ alkoxy,
(14) pyridyl, either unsubstituted or substituted with $C_{1-3}$ alkyl or $C_{1-3}$ alkoxy,
(15) $C_{3-6}$ cycloalkyl,
(16) oxazolyl,
(17) thiazolyl,
(18) triazolyl,
(19) phenoxy or
(20) $C_{2-6}$ alkanoyl.

The term "alkyl" means linear and branched structures and combinations thereof, containing the indicated number of carbon atoms. Examples of alkyl groups include methyl, ethyl, propyl, isopropyl, butyl, s- and t-butyl, pentyl, hexyl and the like.

"Cycloalkyl" means a hydrocarbon having the indicated number of carbon atoms, containing one or more rings. Examples of cycloalkyl groups are cyclopropyl, cyclobutyl, cyclopentyl, cyclohexyl and the like.

"Halogen" or "halo" includes F, Cl, Br, and I unless otherwise specified.

"Heteroaryl" is a 5- or 6-membered aromatic heterocycle, or a benzo- or pyrido-fused version thereof, all having, besides carbon atoms, 1 to 3 hetero atoms selected from N, O, and S as atom(s) constituting the ring. Examples thereof include thienyl, furyl, pyrrolyl, imidazolyl, pyrazolyl, thiazolyl, isothiazolyl, oxazolyl, isoxazolyl, pyridyl, benzothienyl, benzofuranyl, indolyl, pyrimidinyl, pyrazinyl, pyridazinyl, thiadiazolyl, benzoxazolyl, benzothiazolyl, benzopyrazolyl, benzimidazolyl, pyridothiazolyl, quinolyl, isoquinolyl or triazolyl.

"Aryl" is phenyl or naphthyl.

"Alkoxy" means linear and branched structures and combinations thereof, containing the indicated number of carbon atoms. Examples of alkoxy groups include methoxy, ethoxy, propoxy, isopropoxy, butoxy, s- and t-butoxy, pentoxy, and the like.

"Alkanoyl" means linear and branched structures and combinations thereof, containing the indicated number of carbon atoms. Examples of alkanoyl groups include, acetyl, propionyl, butyryl, isobutyryl, valeryl, isovaleryl, pivaloyl and the like.

One embodiment of the novel compounds of this invention is that wherein Ar is phenyl of structural formula I(a)

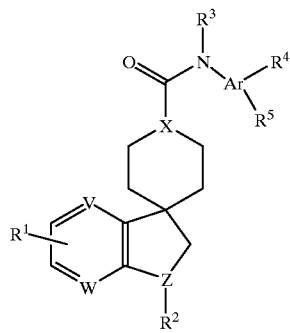

I(a)

or a pharmaceutically acceptable salt thereof.

A class of compounds within this embodiment is that wherein X and Z are both nitrogen, and V and W are both —CH=.

A sub-class is that wherein $R^2$ is —SO$_2$(C$_{1-3}$ alkyl) or —SO$_2$NH$_2$.

A sub-sub-class of the compounds of this embodiment is that wherein $R^4$ and $R^5$ are independently selected from: phenyl, pyridyl, benzoyl, halophenyl, phenoxy, C$_{1-5}$ alkylpyridyl, benzhydryl, phenyl-C$_{1-3}$ alkoxy, NO$_2$, C$_{2-4}$ alkanoyl, halo, C$_{1-5}$ alkoxy, C$_{1-3}$ alkoxycarbonyl, C$_{1-5}$ alkylthio, triazolyl, carboxy, hydrogen, C$_{1-5}$ alkyl, pyridylcarbonyl, and C$_{1-3}$ alkoxyphenyl.

Typical of the compounds of this sub-sub-class are those wherein $R^2$ and phenyl($R^4$)($R^5$) are as shown in the following TABLE I:

TABLE I

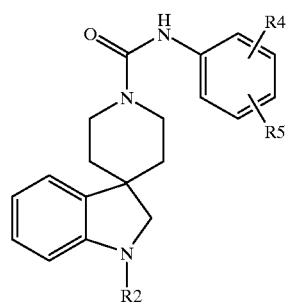

| $R^2$ | 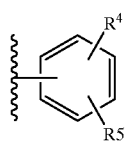 |
|---|---|
| —SO$_2$CH$_3$ | 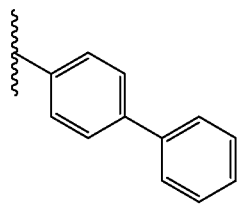 |
| —SO$_2$CH$_3$ | 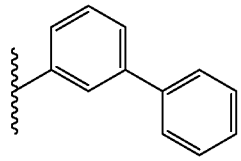 |
| —SO$_2$CH$_3$ | 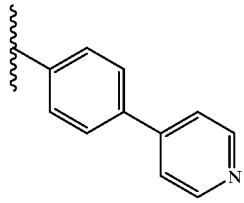 |
| —SO$_2$CH$_3$ | 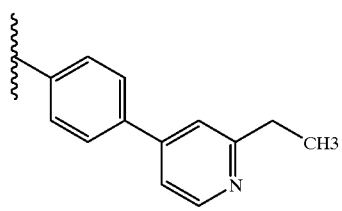 |
| —SO$_2$CH$_3$ | 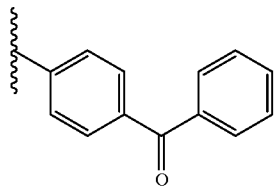 |
| —SO$_2$CH$_3$ | 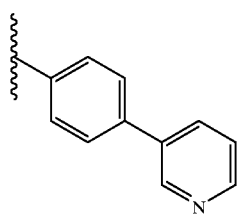 |

| 5 | | | 6 | |
|---|---|---|---|---|
| —SO₂CH₃ | 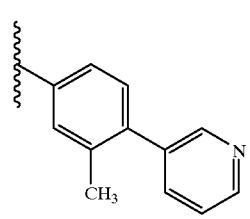 | | —SO₂NH₂ | 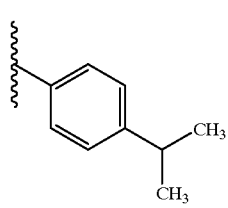 |
| —SO₂CH₃ | 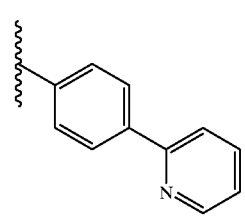 | | —SO₂NH₂ | 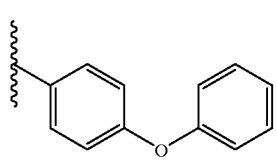 |
| —SO₂CH₃ | 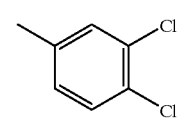 | | —SO₂NH₂ | 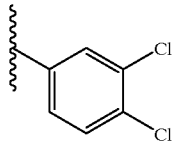 |
| —SO₂CH₃ | 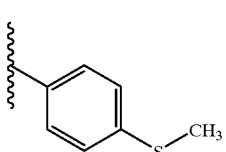 | | —SO₂NH₂ | 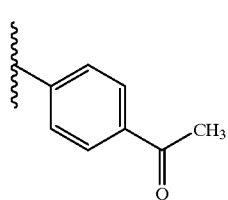 |
| —SO₂CH₃ | 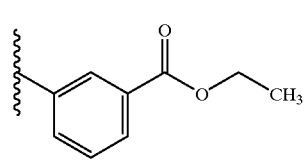 | | —SO₂NH₂ | 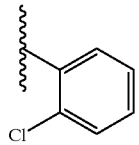 |
| —SO₂C₂H₅ | 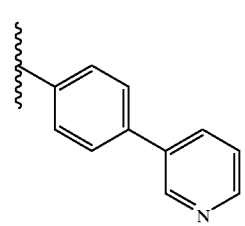 | | —SO₂C₂H₅ | 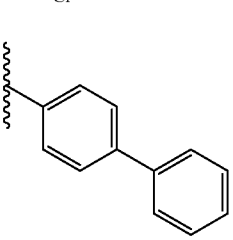 |
| —SO₂CH₃ | 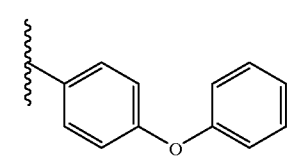 | | —SO₂CH(CH₃)₂ | 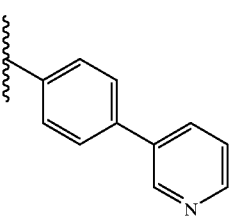 |
| —SO₂CH₃ | 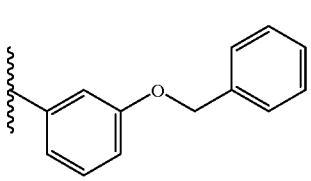 | | —SO₂CH(CH₃)₂ | 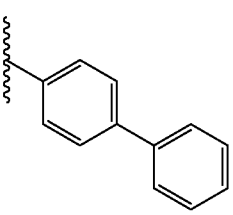 |
| —SO₂NH₂ | 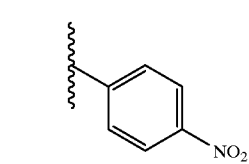 | | | |
A second embodiment of the compounds of this invention is that wherein Ar is a 5- or 6-membered heteroaryl having, besides carbon atoms, 1 to 3 hetero atoms selected from N, O and S as atoms constituting the ring, or benzo- or pyrido-fused versions thereof, of structural formula I(b);

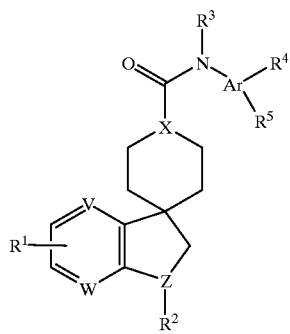

I(b)

or a pharmaceutically acceptable salt thereof.

A class of compounds within this embodiment, is that wherein X and Z are both nitrogen, and V and W are both —CH=.

A sub-class is that wherein $R^2$ is —$SO_2(C_{1-3}$ alkyl) or —$SO_2N(C_{1-3}$ alkyl)$_2$.

A sub-sub-class of compounds within this embodiment is that wherein the heteroaryl group, Ar, is selected from: thiazolyl, thiadiazolyl, pyrazolyl, pyridyl, benzothiazolyl, oxazolyl, pyridothiazolyl, benzoxazolyl, quinolyl, pyrazinyl, thienyl, isoxazolyl, pyrimidinyl, benzimidazolyl, oxadiazolyl and imidazolyl.

Typical of the compounds of this sub-sub-class are those wherein $R^2$ and $Ar(R^4)(R^5)$ are as shown in TABLE II.

TABLE II

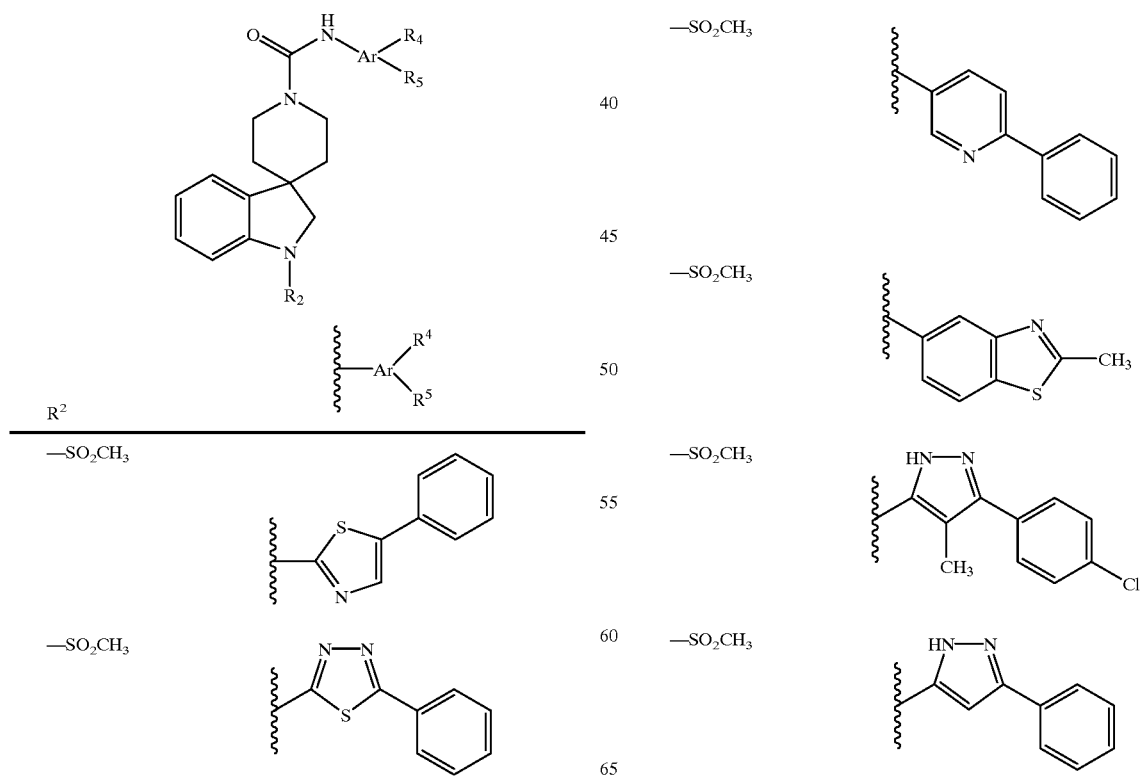

TABLE II-continued

| $R^2$ | Ar with $R^4$, $R^5$ |
|---|---|
| —SO$_2$CH$_3$ | 5-(phenyl)isoxazol-3-yl |
| —SO$_2$NH$_2$ | 4-phenylfuran-2-yl |
| —SO$_2$CH$_3$ | 4-(4-chlorophenyl)thiazol-2-yl |
| —SO$_2$CH$_3$ | 5-(pyridin-3-yl)-1H-pyrazol-3-yl |
| —SO$_2$CH$_3$ | 5-(4-methoxyphenyl)-1H-pyrazol-3-yl |
| —SO$_2$CH$_3$ | 5-(3-methoxyphenyl)-1H-pyrazol-3-yl |

TABLE II-continued

| $R^2$ | Ar with $R^4$, $R^5$ |
|---|---|
| —SO$_2$CH$_3$ | 5-(2-methoxyphenyl)-1H-pyrazol-3-yl |
| —SO$_2$CH$_3$ | 5-(phenyl)isoxazol-3-yl |
| —SO$_2$CH$_3$ | 5-(4-bromophenyl)-1H-pyrazol-3-yl |
| —SO$_2$CH$_3$ | 5-(5-methoxypyridin-3-yl)-1H-pyrazol-3-yl |
| —SO$_2$CH$_3$ | 5-(3-chlorophenyl)-1H-pyrazol-3-yl |
| —SO$_2$CH$_3$ | 5-(2-chlorophenyl)-1H-pyrazol-3-yl |

TABLE II-continued
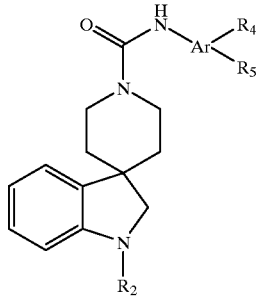
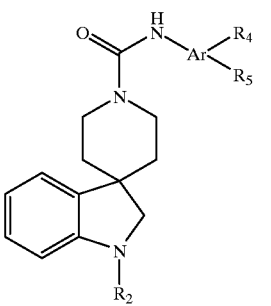
| R² | |
|---|---|
| —SO₂CH₃ | 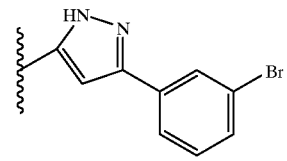 |
| —SO₂CH₃ | 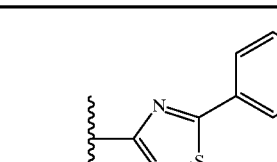 |
| —SO₂CH₃ | 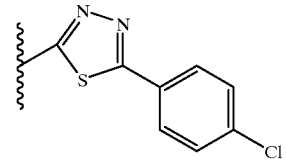 |
| —SO₂CH₃ | 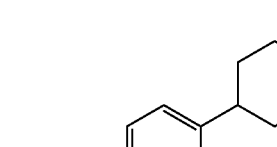 |
| —SO₂CH₃ | 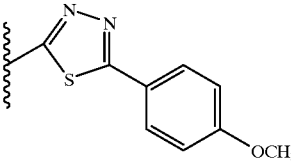 |
| —SO₂CH₃ | 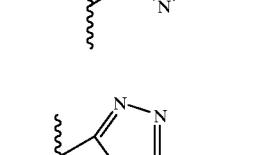 |
| —SO₂CH₃ | 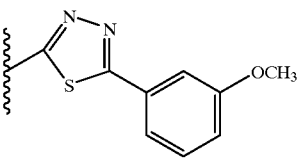 |
TABLE II-continued
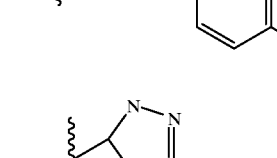
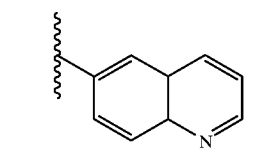
| R² | |
|---|---|
| —SO₂CH₃ | 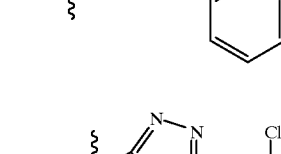 |
| —SO₂CH₃ | 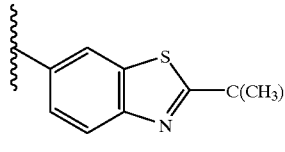 |
| —SO₂CH₃ | 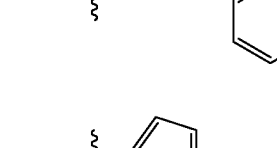 |
| —SO₂CH₃ | 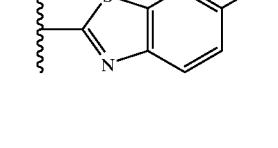 |
| —SO₂CH₃ | 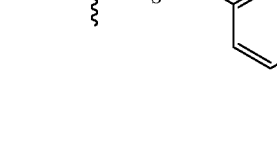 |
| —SO₂CH₃ |  |
| —SO₂CH₃ |  |

TABLE II-continued
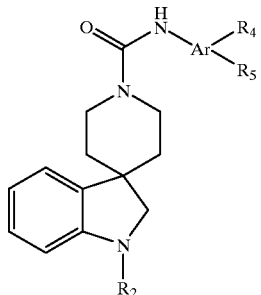
| R² | ⸗Ar⟨R⁴,R⁵ |
|---|---|
| —SO₂CH₃ | 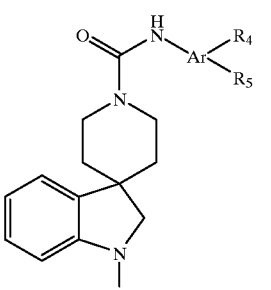 |
| —SO₂CH₃ | 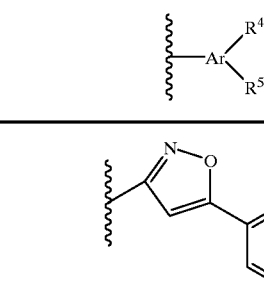 |
| —SO₂CH₃ | 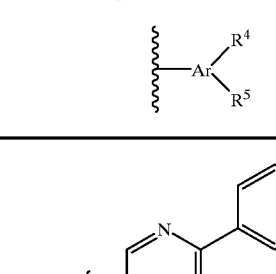 |
| —SO₂CH₃ | 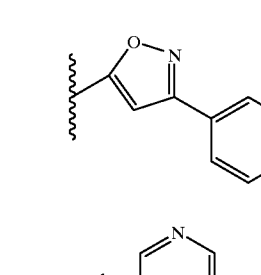 |
| —SO₂CH₃ | 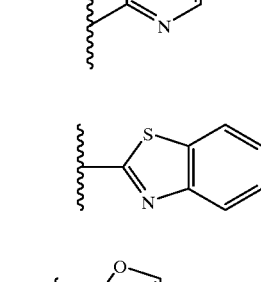 |
| —SO₂CH₃ | 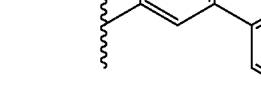 |
| —SO₂CH₃ | 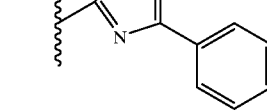 |
TABLE II-continued
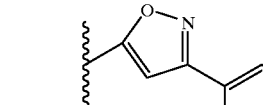
| R² | ⸗Ar⟨R⁴,R⁵ |
|---|---|
| —SO₂CH₃ | 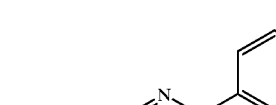 |
| —SO₂CH₃ | 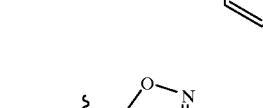 |
| —SO₂CH₃ | 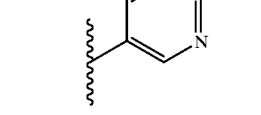 |
| —SO₂CH₃ |  |
| —SO₂N(CH₃)₂ | 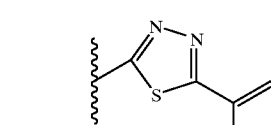 |
| —SO₂NH₂ | 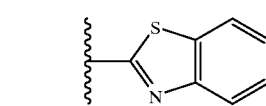 |

TABLE II-continued

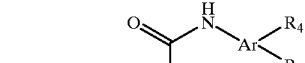

| R² | |
|---|---|
| —SO₂CH₃ | 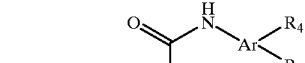 |
| —SO₂C₂H₅ | 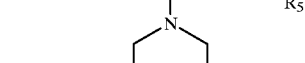 |
| —SO₂C₂H₅ | 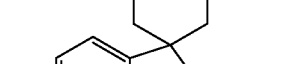 |
| —SO₂CH₃ | 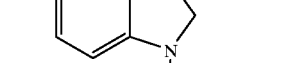 |
| —SO₂CH₃ | 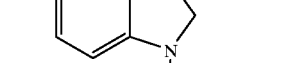 |
| —SO₂C₂H₅ | 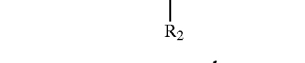 |

TABLE II-continued

| R² | |
|---|---|
| —SO₂C₂H₅ | (pyrazinyl-thiadiazole) |

A third embodiment of the compounds of this invention is that wherein one of X and Z is N and the other is —CH= of structural formula 1(c):

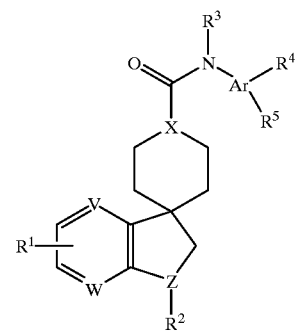

I(c)

or a pharmaceutically acceptable salt thereof.

A class of compounds within this embodiment is that wherein X is N, Z is —CH= and V and W are both —CH=

Typical of the compounds within this class are those shown in TABLE III:

TABLE III

A second class of compounds within this embodiment is that wherein X is —CH=, Z is N and V and W are both —CH=.

Typical of the compounds within this second class are those shown in TABLE IV:

TABLE IV

TABLE IV-continued
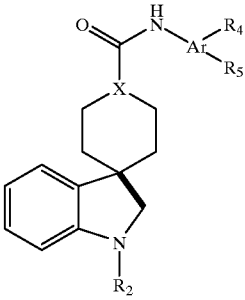
| R² | X | [Ar with R⁴/R⁵] |
|---|---|---|
| —SO₂CH₃ | 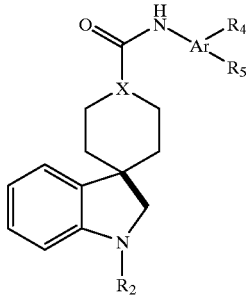 |  |
| —SO₂CH₃ | 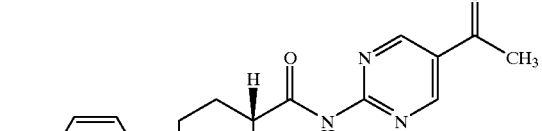 |  |
| —SO₂CH₃ |  |  |
| —SO₂CH₃ | 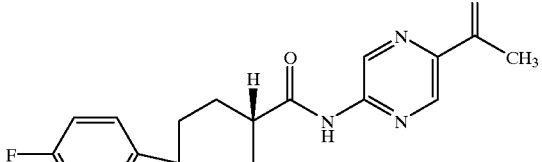 |  |
| —SO₂CH₃ |  |  |
TABLE IV-continued
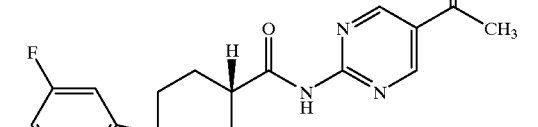
| R² | X | [Ar with R⁴/R⁵] |
|---|---|---|

TABLE IV-continued

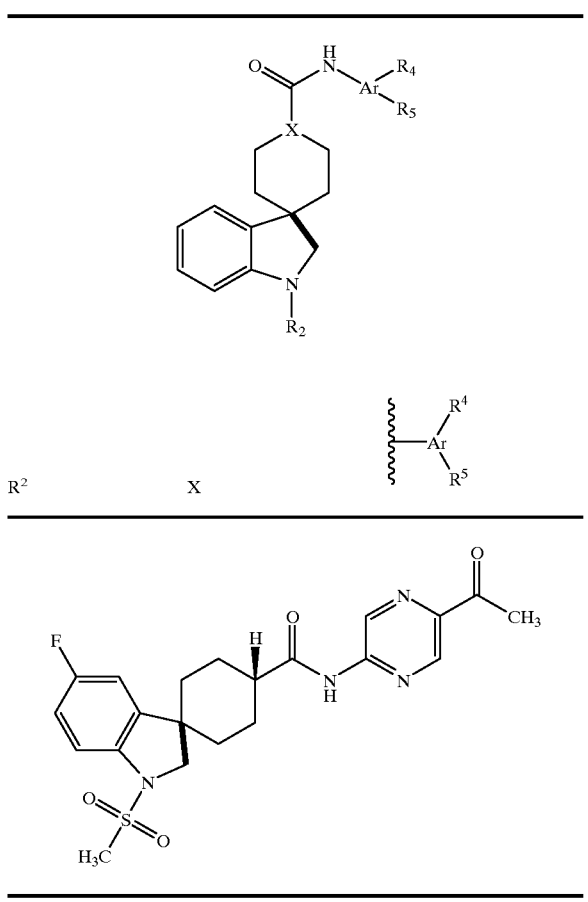

| R² | X | 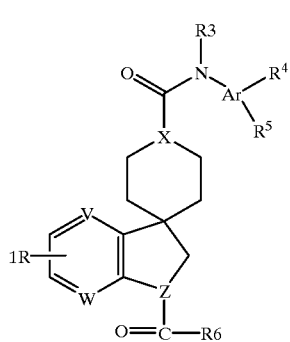 |
|---|---|---|

A fourth embodiment of the compounds of this invention is that wherein R² is —COR⁶ of structural formula I(d):

I(d)

(structure shown)

or a pharmaceutically acceptable salt thereof.

A class of compounds within this embodiment is that wherein X and Z are both N and V and W are both —CH=.

Typical of the compounds within this embodiment are those shown in TABLE V:

TABLE V

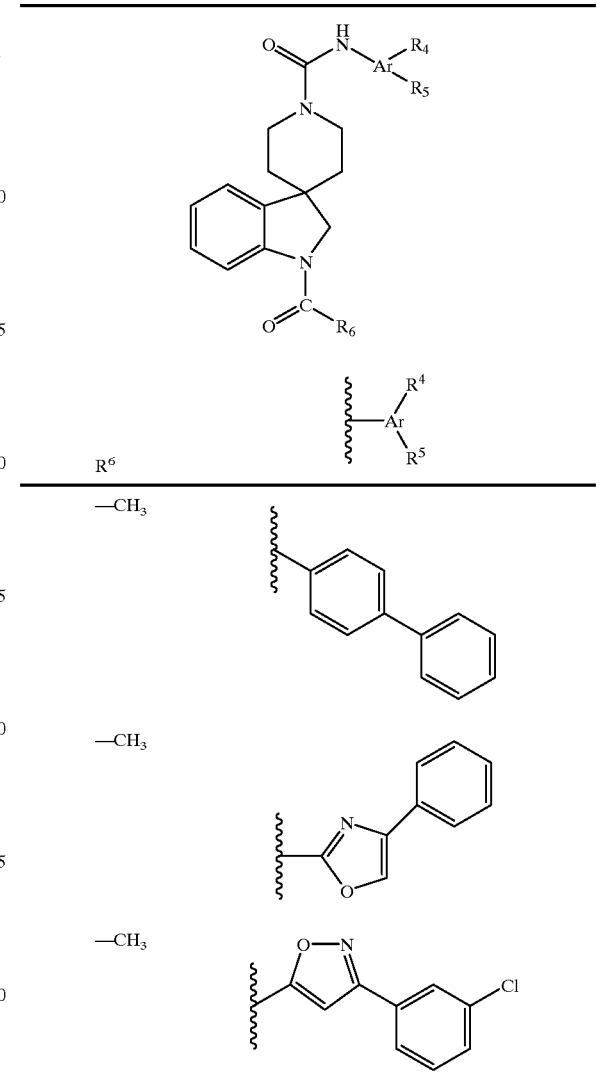

| R⁶ | 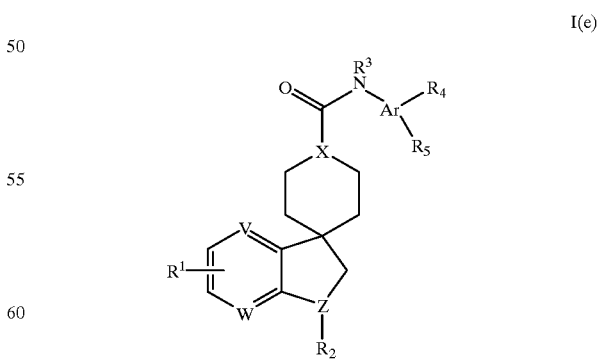 |
|---|---|
| —CH₃ | (biphenyl) |
| —CH₃ | (4-phenyl-oxazole) |
| —CH₃ | (3-(3-chlorophenyl)-isoxazole) |

A fifth embodiment of the compounds of this invention is that wherein one of V or W is nitrogen (N) and the other is —CH= of formula I(e):

I(e)

(structure shown)

A class of compounds within this embodiment is that wherein R¹ and R³ are H and Z are both nitrogen.

A sub-class of compounds within this class is that wherein R² is —SO₂CH₃.

Typical of the compounds within this sub-class are those depicted in the following TABLE VI:

TABLE VI

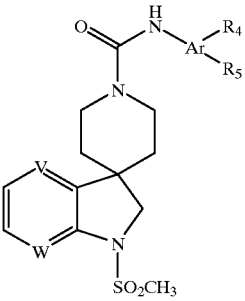

| V | W | |
|---|---|---|
| —N= | —CH= |  |
| —CH= | —N= | 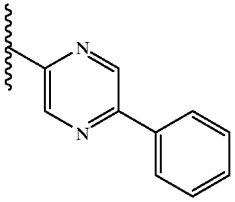 |
| —CH= | —N= | 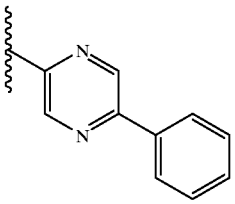 |
| —CH= | —N= | 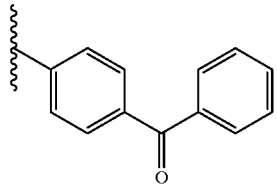 |

Some of the compounds described herein contain one or more asymmetric centers and may thus give rise to diastereomers and optical isomers. The present invention is meant to include such possible diastereomers as well as their racemic and resolved, enantiomerically pure forms and pharmaceutically acceptable salts thereof.

The term "pharmaceutically acceptable salts" refers to salts prepared from pharmaceutically acceptable non-toxic acids or bases including inorganic and organic acids and bases.

When the compound of the present invention is acidic, salts may be prepared from inorganic bases such as aluminum, ammonium, calcium, copper, iron, lithium, magnesium, manganese, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, hydrabamine, N-(2-hydroxyethyl)piperidine, N-(2-hydroxyethyl)pyrrolidine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids. It will be understood that in the materials which follows, references to the compounds of Formula I are meant to also include the pharmaceutically acceptable salts.

Another aspect of this invention are the processes used to prepare the novel compounds.

Compounds in which X and Z are both nitrogen are prepared by the general procedures outlined in Scheme I.

SCHEME I

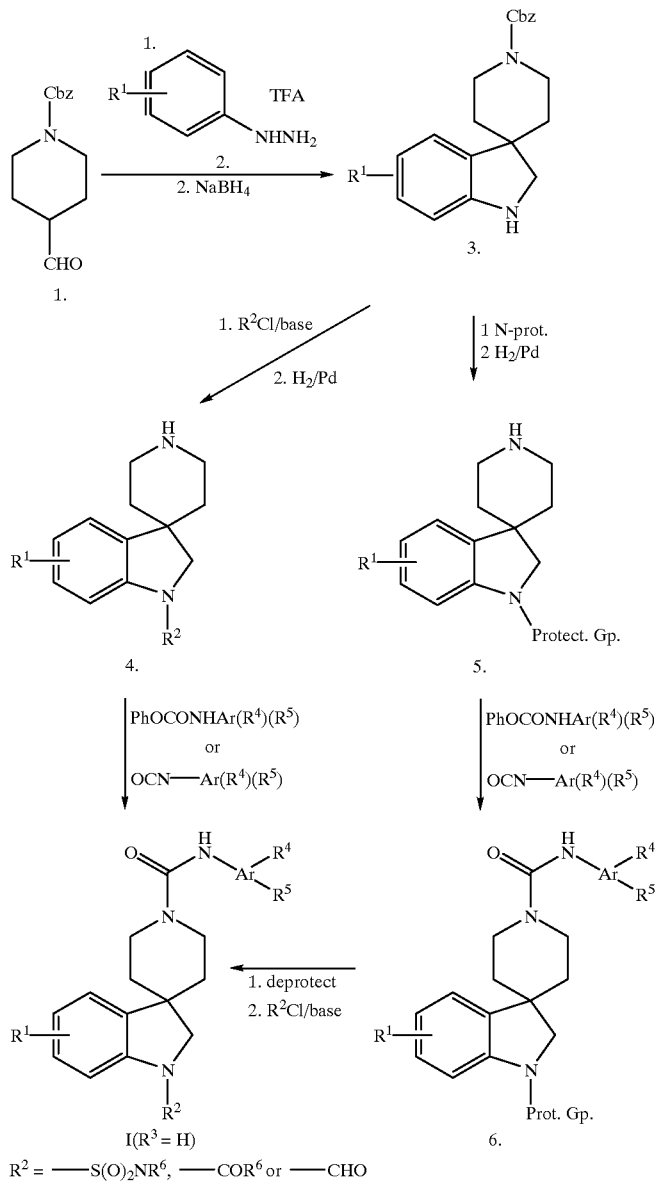

The Cbz spiroindoline 3 is prepared according to the method described in *Tetrahedron* 53, 10983–10992 (1997). In one procedure 3 is treated with a reagent R²Cl, wherein R² is as defined above, in the presence of a base such as a tertiary amine, including triethylamine (Et₃N), diisopropylethylamine (DIEA), or pyridine, followed by removal of the carbobenzyloxy (Cbz) protecting group by hydrogenolysis with hydrogen over a noble metal catalyst at room temperature and pressure in a lower alcohol such as methanol or ethanol, or an etherial solvent such as diethyl ether of tetrahydrofuran (THF) or mixtures thereof to give 4 following the methods described in *Tetrahedron* 53, 10983–10992, (1997) wherein the preparation of 4 is described wherein R² is —SO₂CH₃.

Compound 4 (with R² protected if necessary) is then treated with a phenyl carbamate of structure PHOCONH—Ar(R⁴)(R⁵) in the presence of a tertiary amine in an organic solvent such as a haloalkane such as chloroform, methylene chloride, ethylene dichloride or the like at reflux temperature or in the presence of NaOH in H₂O/DMSO, until the reaction is complete, usually in about ½ to about 3 hours followed by deprotection of the R² group if necessary, to provide the Compound I(R³=H).

In the above procedures, the phenyl carbamates are prepared by reaction of the corresponding amines of structure NH₂—Ar(R⁴)(R⁵) which are commercially available or readily synthesized, with phenyl chloroformate in pyridine at room temperature as described in Example I below.

Alternatively, Compound I is prepared by treatment of 4 with an isocyanate of structure OCN—Ar(R⁴)(R⁵) in a chlorinated alkane at reflux temperature until the reaction is complete in about 4 to about 12 hours.

Compound I can also be prepared by conducting the above procedures in the reverse order. The indoline nitrogen of 3 is protected with Boc by treatment with di-tert-butyl dicarbonate in the presence of a base, such as, NaOH or triethyl amine, in an inert solvent such as aqueous dioxane or methanol and the Cbz group is hydrogenolyzed with hydrogen and a noble metal catalyst to give 5. Treatment of 5 with either the phenyl carbamate or isocyanate described earlier provides 6 which upon deprotecting with a strong acid such as hydrochloric or trifluoroacetic acid in an inert solvent such as ethyl acetate or methylene chloride and treatment with $R^2Cl$ in the presence of a tertiary amine as described above provides Compound $I(R^3=H)$.

Compounds of this invention are antagonists of the Y5 receptor and as such are useful for the prevention and treatment of disorders or diseases associated with the Y5 receptor sub-type, preferably for the treatment of feeding disorders such as obesity, anorexia nervosa and bullimia nervosa, and other abnormal conditions, such as diabetes, hypertension, hyperlipemia, hypercholesterolenia, congestive heart failure, renal dysfunction, sexual/reproductive disorders, depression, anxiety, shock, epileptic seizure, memory loss, sleep disturbance, pain, migraine, cerebral hemorrhage, nasal congestion, gastrointestinal disorders, arthritis and immunodeficiency syndrome.

The Y5 antagonists of this invention may also be used in combination with other anti-obesity agents for increased efficacy in the prevention and treatment of obesity. Such agents would include, but not be limited to: sibutramine; dexenfluramine; leptin; growth hormone secretagogues such as those disclosed and specifically described in U.S. Pat. No. 5,536,716; melanocortin agonists such as Melanotan II; Beta-3 agonists such as those disclosed and specifically described in patent publications WO94/18161, WO95/29159, WO97/46556, WO98/04526 and WO98/32753; 5HT-2 agonists; orexin antagonists; melanin concentrating hormone antagonists; galanin antagonists; CCK agonists; GLP-1 agonists; corticotropin-releasing hormone agonists; and Y1 antagonists.

The method of treatment of this invention comprises a method of antagonizing the Y5 receptor and treating Y5 receptor mediated diseases by administering to a patient in need of such treatment a non-toxic therapeutically effective amount of a compound of this invention that selectively antagonizes the Y5 receptor in preference to the other NPY receptors.

Dosage levels of the order of from about 0.01 mg to about 140 mg/kg of body weight per day are useful in the treatment of the above-indicated conditions, or alternatively about 0.5 mg to about 7 g per patient per day. For example, obesity may be effectively prevented or treated by the administration of from about 0.01 to 50 mg of the compound per kilogram of body weight per day, or alternatively about 0.5 mg to about 3.5 g per patient per day.

For the treatment of any of these Y5 receptor mediated diseases, compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The novel pharmaceutical compositions of this invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of a suppository for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following Examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Abbreviations, used herein have the following meanings:

| ABBREVIATION | DEFINITION |
| --- | --- |
| Ac | acetyl |
| Boc | t-butoxycarbony |
| BSA | bovine serum albumin |
| MCPBA | m-chloroperbenzoic acid |
| Cbz | carbobenzyloxy |
| Et | ethyl |
| HEPES | [4-(2-hydroxyethyl)-1-piperazineethane sulfonic acid] |
| IPE | isopropyl ether |
| Me | methyl |
| PCC | pyridium chlorochromate |
| PhMe-MeCN | toluene acetonitrile |
| PMSF | toluene sulfonylfluoride |
| WSC.HCl | water soluble carbodiimide.HCl |

EXAMPLE 1

1-Methanesulfonyl-N-(5-phenyl-2-pyrazinyl)spiro[indoline-3,4'-piperidine]-1'-carboxamide 100

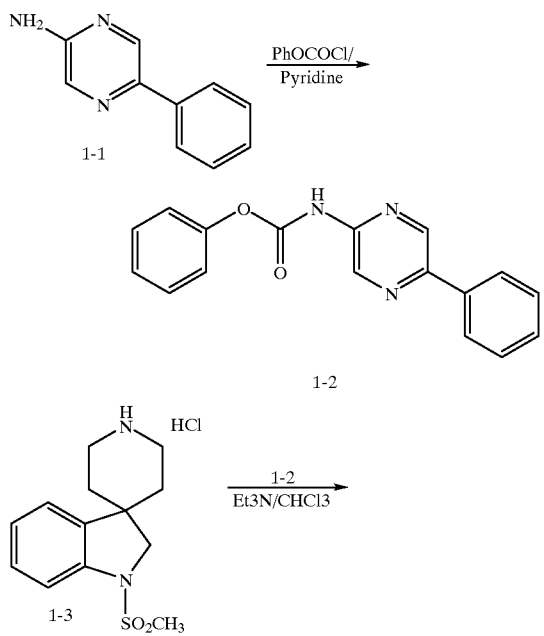

-continued

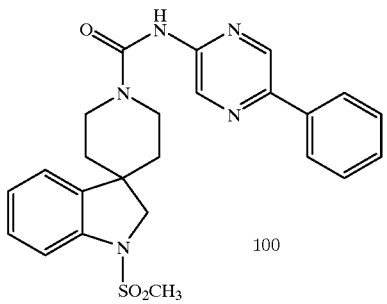

100

Step 1: Preparation of Compound 1-2

Phenyl chloroformate (0.64 mL, 5.1 mmol) was added to a vigorously stirred solution of 2-amino-5-phenylpyrazine 1-1 (794 mg, 4.64 mmol) in pyridine (10 mL) at room temperature. After being stirred at room temperature overnight, the mixture was diluted with EtOAc to give a suspension, in which the desired compound precipitated out. The suspension was successively washed with 1 N KHSO$_4$, brine and dist. water. The precipitate was collected by filtration and dried to give phenyl N-(5-phenyl-2-pyrazinyl) carbamate 1-2 (847 mg, 63%). The filtrate was concentrated under reduced pressure to produce precipitate, which was collected and dried to give the second crop (340 mg, 25%).

Step 2: Preparation of Compound 100

A mixture of phenyl N-(5-phenyl-2-pyrazinyl)carbamate 1-2 (7,350 mg, 1.20 mmol), 1-methylsulfonylspiro[indoline-3,4'-piperidine]hydrochloride 1-3 (400 mg, 1.32 mmol) and Et3N (0.5 mL, 3.6 mmol) in CHCl3 (6 mL) was heated to reflux for 3 h. After cooling, the mixture was diluted with EtOAc, washed with 10% citric acid, sat. NaHCO$_3$ and brine, dried over MgSO$_4$, and concentrated under reduced pressure to start precipitation. The precipitate was collected by filtration and dried in vacuo to give 100 (517 mg, 93%) as a white powder.

m.p.: 201–203° C.

1H-NMR (DMSO-d6) was consistent with the proposed title structure. FABMS: 464 (M+H)

Compounds #101–#137 were prepared from 1-methylsulfonylspiro[indoline-3,4'-piperidine] hydrochloride and the appropriate phenyl carbamates according to the procedure described in Example 1.

101
N-[5-(3-fluorophenyl)-2-pyrazinyl]-1-methylsulfonylspiro[indoline-3,4'-piperidine]-1'-carboxamide
m.p.: 203–205° C.

102
N-[5-(2-methoxyphenyl)-2-pyrazinyl]-1-methylsulfonylspiro[indoline-3,4'-piperidine]-1'-carboxamide
m.p.: 186–188° C.

103
N-[5-(2-chlorophenyl)-2-pyrazinyl]-1-methylsulfonylspiro[indoline-3,4'-piperidine]-1'-carboxamide
m.p.: 197–199° C.

104
1-methylsulfonyl-N-[5-(2-pyridyl)-2-pyrazinyl]spiro[indoline-3,4'-piperidine]-1'-carboxamide
m.p.: 234–235° C.

105
1-methylsulfonyl-N-[5-(2-propenyl)-2-pyrazinyl]spiro[indoline-3,4'-piperidine]-1'-carboxamide
m.p.: 180.5–182.7° C.

106
1-methylsulfonyl-N-[4-(1-mehtyl-2-imidazolyl)phenyl]spiro[indoline-3,4'-piperidine]-1'-carboxamide hydrochloride
m.p.: 196–198° C.

107
N-[4-(2-ethyl-4-thiazolyl)phenyl]-1-methylsulfonylspiro[indoline-3,4'-piperidine]-1'-carboxamide
m.p.: 242–242.5° C.

108
1-methylsulfonyl-N-[4-(4-pyridyl)phenyl]spiro[indoline-3,4'-piperidine]-1'-carboxamide
m.p.: 272–274° C.

109
N-[4-(2-ethyl-4-pyridyl)phenyl]-1-methylsulfonylspiro[indoline-3,4'-piperidine]-1'-carboxamide hydrochloride
m.p.: 220–222° C.

110
N-(4-benzoylphenyl)-1-methylsulfonylspiro[indoline-3,4'-piperidine]-1'-carboxamide hydrochloride
m.p.: 222–225° C.

111
1-methylsulfonyl-N-[4-(2-thiazolyl)phenyl]spiro[indoline-3,4'-piperidine]-1'-carboxamide
m.p.: 143.2–147.4° C.

112
1-methylsulfonyl-N-(5-phenyl-2-pyridyl)spiro[indoline-3,4'-piperidine]-1'-carboxamide
m.p.: 214° C.

113
1-methylsulfonyl-N-(2-phenyl-5-pyrimidinyl)spiro[indoline-3,4'-piperidine]-1'-carboxamide
m.p.: 251–253° C.

114
1-methylsulfonyl-N-(2-phenyl-5-pyridyl)spiro[indoline-3,4'-piperidine]-1'-carboxamide
m.p.: 224° C.

115
1-methylsulfonyl-N-(5-phenyl-2-pyrimidinyl)spiro[indoline-3,4'-piperidine]-1'-carboxamide
m.p.: 122–123° C.

116
1-methylsulfonyl-N-[2-(1-pyrrolidinyl)-5-pyridyl]spiro[indoline-3,4'-piperidine]-1'-carboxamide
m.p.: 252–254° C.

117
N-[5-(4-chlorophenyl)pyrrazol-3-yl]-1-methylsulfonylspiro[indoline-3,4'-piperidine]-1'-carboxamide
m.p.: 152–156° C.

118
N-[5-(5-methoxy-3-pyridyl)pyrrazol-3-yl]-1-methylsulfonylspiro[indoline-3,4'-piperidine]-1'-carboxamide
m.p.: 213–215° C.

119
1-methylsulfonyl-N-(4-phenyloxazol-2-yl)spiro[indoline-3,4'-piperidine]-1'-carboxamide
m.p.: 189–192° C.

120
N-[5-(3-methoxyphenyl)pyrrazol-3-yl]-1-methylsulfonylspiro[indoline-3,4'-piperidine]-1'-carboxamide
m.p.: 158–160° C.

121
1-methylsulfonyl-N-(3-phenylisoxazol-5-yl)spiro[indoline-3,4'-piperidine]-1'-carboxamide m.p.: 235–237° C.

122
N-[5-(3-chlorophenyl)pyrrazol-3-yl]-1-methylsulfonylspiro[indoline-3,4'-piperidine]-1'-carboxamide
m.p.: 185–187° C.

123
1-methylsulfonyl-N-(5-phenyl-1,2,4-thiadiazol-3-yl)spiro[indoline-3,4'-piperidine]-1'-carboxamide
m.p.: 133–136° C.

124
N-[4-(3-methoxyphenyl)oxazol-2-yl]-1-methylsulfonylspiro[indoline-3,4'-piperidine]-1'-carboxamide colorless amorphous solid.
1H-NMR (DMSO-d6) ppm:1.62–1.87 (4 H, m), 2.96–3.09 (2 H, m), 3.05 (3 H, s), 3.78 (3 H, s), 3.92 (2 H, s), 4.04–4.16 (2 H, m), 6.87 (1 H, m), 7.04 (1 H, m), 7.19–7.37 (7 H, m), 8.35 (1 H, br s).

125
1-methylsulfonyl-N-(5-phenylpyrrazol-3-yl)spiro[indoline-3,4'-piperidine]-1'-carboxamide
m.p.: 163° C.

126
N-[1-(3-methoxyphenyl)imidazol-4-yl]-1-methylsulfonylspiro[indoline-3,4'-piperidine]-1'-carboxamide
m.p.: 216–218° C.

127
N-[1-(3-chlorophenyl)imidazol-4-yl]-1-methylsulfonylspiro[indoline-3,4'-piperidine]-1'-carboxamide
m.p.: 232–234° C.

128
N-(4-methoxybenzoxazol-2-yl)-1-methylsulfonylspiro[indoline-3,4'-piperidine]-1'-carboxamide
m.p.: 195–199° C.

129
N-(5-fluorobenzothiazol-2-yl)-1-methylsulfonylspiro[indoline-3,4'-piperidine]-1'-carboxamide
m.p.: 243–244° C.

130
1-methylsulfonyl-N-(6-methylquinoxalin-2-yl)spiro[indoline-3,4'-piperidine]-1'-carboxamide
m.p.: 224–225° C.

131
1-methylsulfonyl-N-(8-methylquinolin-2-yl)spiro[indoline-3,4'-piperidine]-1'-carboxamide
m.p.: 219–220° C.

132
N-(7-chloroquinoxalin-2-yl)-1-methylsulfonylspiro[indoline-3,4'-piperidine]-1'-carboxamide
m.p.: 213–214° C.

133
N-(6-methoxypyrido[2,2-d]thiazol-2-yl)-1-methylsulfonylspiro[indoline-3,4'-piperidine]-1'-carboxamide
m.p.: 179–182° C.

134
N-(5-methoxybenzoxazol-2-yl)-1-methylsulfonylspiro[indoline-3,4'-piperidine]-1'-carboxamide
m.p.: 194–196° C.

135
N-(5-chlorobenzoazol-2-yl)-1-methylsulfonylspiro[indoline-3,4'-piperidine]-1'-carboxamide
m.p.: 172–176° C.

136
1-methylsulfonyl-N-(1,5-naphthyridin-2-yl)spiro[indoline-3,4'-piperidine]-1'-carboxamide pale yellow amorphous solid.
1H-NMR (DMSO-d6) ppm:1.64–1.92 (4 H, m), 2.95–3.16 (2 H, m), 3.05 (3 H, s), 3.93 (2 H, s), 4.18–4.30 (2 H, m), 7.04 (1 H, m), 7.18–7.37 (3 H, m), 7.66 (1 H, dd, J=4.3, 8.5 Hz), 8.14 (1 H, m), 8.22–8.30 (2 H, m), 8.80 (1 H, m), 9.84 (1 H, br s).

137
N-(4-methylbenzothiazol-2-yl)-1-methylsulfonylspiro[indoline-3,4'-piperidine]-1'-carboxamide
m.p.: 182–183° C.

Compound #138 was prepared from 7-fluoro-1-methylsulfonylspiro[indoline-3,4'-piperidine]hydrochloride [prepared in analogy to the method described in U.S. Pat. No. 5,536,716] and phenyl N-(5-phenyl-2-pyrazinyl) carbamate according to the procedure described in Example 1.

138
7-fluoro-1-methylsulfonyl-N-(5-phenyl-2-pyrazinyl)spiro[indoline-3,4'-piperidine]-1'-carboxamide pale yellow amorphous solid.
1H-NMR (CDCl3) δ ppm: 1.62–1.96 (4 H, m), 3.09–3.18 (2 H, m), 3.33 (3 H, s), 4.14–4.26 (2 H, m), 6.93–7.10 (3 H, m), 7.90 (1 H, brs), 7.97(2 H, d, J=6.8 Hz), 8.56 (1 H, s), 9.54 (1 H, d, J=2.3 Hz).

Compound #139 was prepared from 6-fluoro-1-methylsulfonylspiro[indoline-3,4'-piperidine]hydrochloride [prepared in analogy to the method described in U.S. Pat. No. 5,536,716] and phenyl N-(5-phenyl-2-pyrazinyl) carbamate according to the procedure described in Example 1.

139
6-fluoro-1-methylsulfonyl-N-(5-phenyl-2-pyrazinyl)spiro[indoline-3,4'-piperidine]-1'-carboxamide
m.p.: 234–237° C.

Compounds #140–#144 were prepared from 1-ethylsulfonylspiro[indoline-3,4'-piperidine]hydrochloride [prepared in analogy to the method described in U.S. Pat. No. 5,536,716] and the corresponding phenyl carbamates according to the procedure described in Example 1.

140
1-ethylsulfonyl-N-(1-phenylimidazol-4-yl)spiro[indoline-3,4'-piperidine]-1'-carboxamide hydrochloride
m.p.: 139–140° C.

141
N-(4-benzoylphenyl)-1-ethylsulfonylspiro[indoline-3,4'-piperidine]-1'-carboxamide pale yellow amorphous solid.
1H-NMR (CDCl3) δ ppm: 1.44 (3 H, t, J=7.4 Hz), 1.80–1.85 (2 H, m), 1.95–2.04 (2 H, m), 3.10–3.20 (2 H, m), 3.17 (2 H, t, J=7.4 Hz), 3.97 (2 H, s), 4.11–4.16 (2 H, m), 6.8–6.9 (1 H, brs), 7.08 (1 H, t, J=7.3 Hz), 7.16 (1 H, d, J=8.1 Hz), 7.23 (1 H, d, J=8.1 Hz), 7.37 (1 H, d, J=8.1 Hz), 7.48–7.58 (5 H, m), 7.76–7.83 (4 H, m).

142
N-[5-(4-chlorophenyl)pyrrazol-3-yl]-1-ethylsulfonylspiro[indoline-3,4'-piperidine]-1'-carboxamide
m.p.: 249.0–249.8° C.

143
N-[5-(4-chlorophenyl)isoxazol-3-yl]-1-ethylsulfonylspiro[indoline-3,4'-piperidine]-1'-carboxamide
m.p.: 178.3–178.5° C.

144
1-ethylsulfonyl-N-[1-(3-methoxyphenyl)imidazol-4-yl]spiro[indoline-3,4'-piperidine]-1'-carboxamide pale yellow amorphous solid
1H NMR (CDCl3) δ ppm: 1.43 (3 H, t, J=7.5 Hz), 1.75–1.82 (2 H, m), 1.89–2.00 (2 H, m), 3.01–3.13 (2 H, m), 3.16 (2 H, q, J=7.5 Hz), 3.85 (3 H, s), 3.96 (2 H, s), 4.10–4.20 (2 H, m), 6.86–6.90 (1H, m), 6.93–6.95 (1H, m), 6.98–7.07 (2 H, m), 7.14 (1 H, d, J=7.5 Hz), 7.22 (1 H, t, J=7.5 Hz), 7.33–7.41 (3 H, m), 7.56 (1 H, s), 7.60 (1 H, s).

Compound #145 was prepared from 1-ethylsulfonyl-5-fluorospiro[indoline-3,4'-piperidine]hydrochloride [prepared in analogy to the method described in U.S. Pat. No. 5,536,716] and phenyl N-(1-phenylimidazol-4-yl) carbamate according to the procedure described in Example 1.

145
1-ethylsulfonyl-5-fluoro-N-(1-phenylimidazol-4-yl)spiro[indoline-3,4'-piperidine]-1'-carboxamide hydrochloride
m.p.: 140–141° C.

146
1-methylsulfonyl-N-[5-(1,3,4-thiadiazol-2-yl)-2-pyrazinyl]spiro[indoline-3,4'-piperidine]-1'-carboxamide
m.p.: 247–249° C.

147
1-methylsulfonyl-N-[5-(1,2,4-thiadiazol-5-yl)-2-pyrazinyl]spiro[indoline-3,4'-piperidine]-1'-carboxamide
m.p.: 234–238° C.

148
6-fluoro-1-methylsulfonyl-N-[5-(1,3,4-thiadiazol-2-yl)-2-pyrazinyl]spiro[indoline-3,4'-piperidine]-1'-carboxamide
m.p.: 242–243° C.

149
6-fluoro-1-methylsulfonyl-N-[5-(1,2,4-thiadiazol-5-yl)-2-pyrazinyl]spiro[indoline-3,4'-piperidine]-1'-carboxamide
m.p.: 237–239° C.

Compounds #150 and #151 were prepared from 5-fluoro-1-methylsulfonylspiro[indoline-3,4'-piperidine] hydrochloride [prepared in analogy to the method described in U.S. Pat. No. 5,536,716] and the corresponding phenyl carbamates according to the procedure described in Example 1.

150
5-fluoro-1-methylsulfonyl-N-[5-(1,3,4-thiadiazol-2-yl)-2-pyrazinyl]spiro[indoline-3,4'-piperidine]-1'-carboxamide
m.p.: 262–266° C.

151
5-fluoro-1-methylsulfonyl-N-[5-(1,2,4-thiadiazol-5-yl)-2-pyrazinyl]spiro[indoline-3,4'-piperidine]-1'-carboxamide
m.p.: 239–240° C.

152
1-ethylsulfonyl-N-[5-(1,3,4-thiadiazol-2-yl)-2-pyrazinyl]spiro[indoline-3,4'-piperidine]-1'-carboxamide
m.p.: 193–194° C.

153
1-ethylsulfonyl-N-[5-(1,2,4-thiadiazol-5-yl)-2-pyrazinyl]spiro[indoline-3,4'-piperidine]-1'-carboxamide
m.p.: 211–214° C.

Compound #154 was prepared from 1-ethylsulfonyl-6-fluorospiro[indoline-3,4'-piperidine]hydrochloride [prepared in analogy to the method described in U.S. Pat. No. 5,536,716] and phenyl N-[5-(1,3,4-thiadiazol-2-yl)-2-pyrazinyl]carbamate according to the procedure described in Example 1.

154
1-ethylsulfonyl-6-fluoro-N-[5-(1,3,4-thiadiazol-2-yl)-2-pyrazinyl]spiro[indoline-3,4'-piperidine]-1'-carboxamide
m.p.: 228–230° C.

155
1-ethylsulfonyl-5-fluoro-N-[5-(1,3,4-thiadiazol-2-yl)-2-pyrazinyl]spiro[indoline-3,4'-piperidine]-1'-carboxamide
m.p.: 223–224° C.

EXAMPLE 2

N-(2-benzothiazolyl)-1-methylsulfonylspiro[indoline-3,4'-piperidine]-1'-carboxamide 200

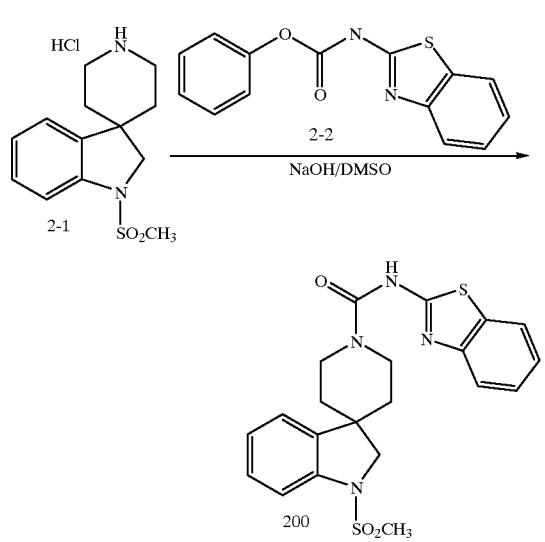

10 M aqueous NaOH solution (75 uL,) was added to a solution of 1-methylsulfonylspiro[indoline-3,4'-piperidine] hydrochloride 2-1(225 mg, 0.74 mmol) in DMSO (2.5 mL). Phenyl N-(2-benzothiazolyl)carbamate 2-2 (200 mg, 0.74 mmol) was added to the mixture, and the resulting mixture was stirred at room temperature for 20 h. The mixture was diluted with water and extracted with EtOAc. The organic extract was washed with dil. NaOH and brine, and dried over $Na_2SO_4$. The solvent was evaporated, and the residue was purified by silica gel column chromatography to give 200 (279 mg, 85%) as a colorless amorphous solid.

1H-NMR (CDCl3) δ ppm: 1.72–1.84 (2 H, m), 1.88–2.00 (2 H, m), 2.92 (3 H, s), 3.06 (2 H, t, J=13.0 Hz), 3.86 (2 H, s), 4.23–4.33 (2 H, m), 7.03–7.16 (2 H, m), 7.20–7.28 (3 H, m), 7.38–7.42 (2 H, m), 7.51–7.61 (1 H, m), 7.70–7.75 (1 H, m).

FABMS: 443 (M+H)

Compound #201 was prepared from 1-methylsulfonylspiro[indoline-3,4'-piperidine] hydrochloride [prepared by the method described in U.S. Pat. No. 5,536,716] and phenyl N-(3-biphenylyl)carbamate according to the procedure described in Example 2.

201
N-3-biphenyl-1-methylsulfonylspiro[indoline-3,4'-piperidine]-1'-carboxamide
m.p.: 211–212° C.

Compound #202 was prepared from 5-fluoro-1-methylsulfonylspiro[indoline-3,4'-piperidine]hydrochloride [prepared in analogy to the method described in U.S. Pat. No. 5,536,716] and phenyl N-(5-phenyl-2-pyrazinyl) carbamate according to the procedure described in Example 2.

202
5-fluoro-1-methylsulfonyl-N-(5-phenyl-2-pyrazinyl) spiro[indoline-3,4'-piperidine]-1'-carboxamide
m.p.: 215.5–215.8° C.

Compound #203 and #204 were prepared from 1-ethylsulfonylspiro[indoline-3,4'-piperidine]hydrochloride [prepared in analogy to the method described in U.S. Pat. No. 5,536,716] and phenyl N-[1-(3-fluorophenyl)-4-imidazolyl]carbamate or phenyl N-[1-(2-fluorophenyl)-4-imidazolyl]carbamate, respectively, according to the procedure described in Example 2.

203

1-ethylsulfonyl-N-[1-(3-fluorophenyl)imidazol-4-yl]spiro[indoline-3,4'-piperidine]-1'-carboxamide m.p.: 200–202° C.

204

1-ethylsulfonyl-N-[1-(2-fluorophenyl)imidazol-4-yl]spiro[indoline-3,4'-piperidine]-1'-carboxamide m.p.: 180–181.5° C.

EXAMPLE 3

N-(4-acetylphenyl)-1-sulfamoylspiro[indoline-3,4'-piperidine]-1'-carboxamide 300

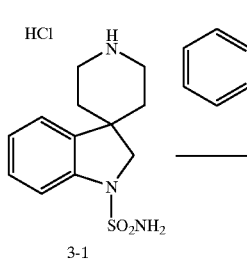 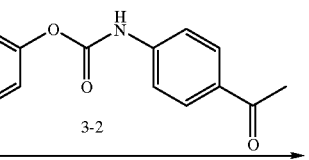

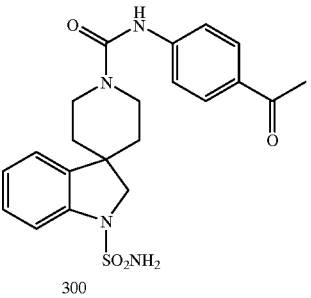

300

1-sulfamoylspiro[indoline-3,4'-piperidine]hydrochloride 3-1 was prepared by the procedure described in WO 9602530.

To a suspension of 1-sulfamoylspiro[indoline-3,4'-piperidine]hydrochloride 3-1 (100 mg, 0.33 mmol) and phenyl 4-acetylphenylcarbamate 3-2 (92 mg, 0.36 mmol) in CHCL$_3$ (3 mL) was added Et$_3$N (0.23 mL, 1.65 mmol) at room temperature. The reaction mixture was heated to reflux for 1 h. The resulting suspension was cooled to room temperature. The resulting suspension was filtered and the filter cake was washed with CHCl$_3$ to give 300 (47 mg, 33%) as a white solid.

m.p.: 233–236° C.

1H-NMR (DMSO-d6) was consistent with the proposed title structure. FABMS: 429 (M+H)

EXAMPLE 4

N-(5-phenyl-1,3,4-thiadiazol-2-yl)-1-sulfamoylspiro[indoline-3,4'-piperidine]-1'-carboxamide 400

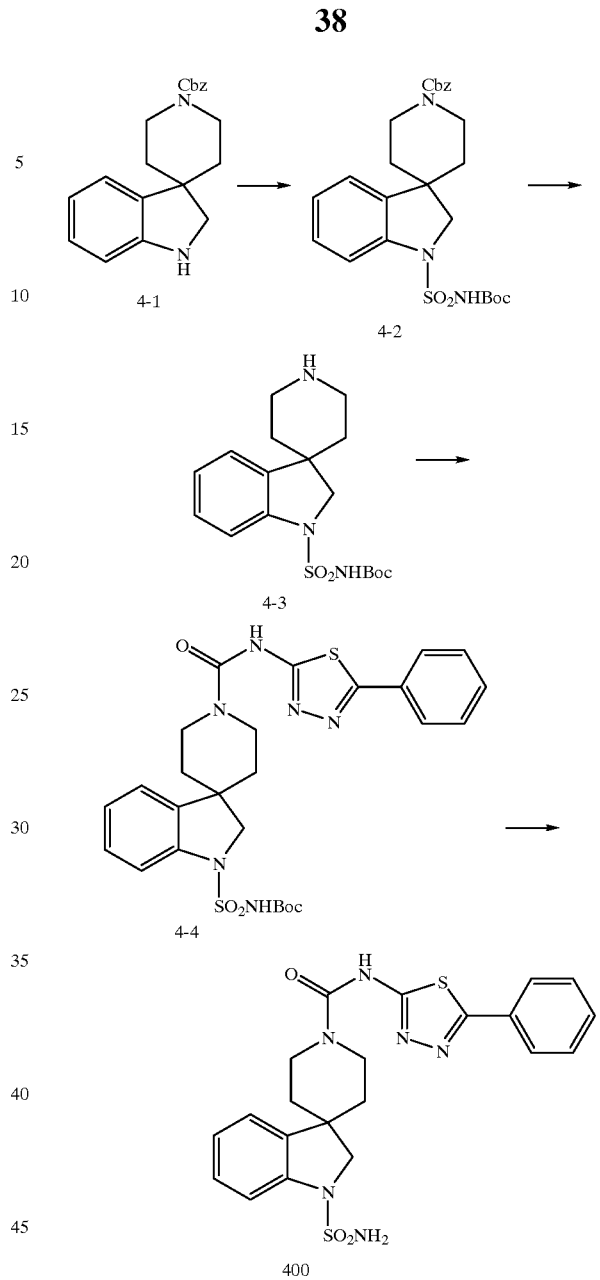

Step 1: Preparation of compound 4-2

Chlorosulfonyl isocyanate (2.70 mL, 31.1 mmol) was added to a stirred solution of tert-butyl alchol (2.96 mL, 31.1 mmol) in EtOAc (400 mL) at −40° C., and the resulting mixture was stirred at −20° C. for 20 min. The mixture was cooled to −78° C., and a solution of 4-1 (5.00 g, 15.5 mmol) in EtOAc (40 mL) was added to the reaction mixture. The mixture was allowed to warm to room temperature and stirred for 14 h. The reaction mixture was washed with sat.NaHCO$_3$, H$_2$O and brine, dried (Na$_2$SO$_4$), and concentrated. The residual oil was purified by silica gel column chromatography (80 g, hexane-EtOAc 4:13:12:1) to give 4-2 (2.13 g, 27%).

Step 2: Preparation of compound 4-3

A mixture of compound 4-2 (411 mg, 0.820 mol) and 20% Pd(OH)$_2$—C (200 mg) in THF (4 mL) and MeOH (4 mL) was stirred under atmospheric pressure of hydrogen for 3 h. The catalyst was filtered off, and the filtrate was concentrated to give compound 4-3 (215 mg, 71%).

Step 3: Preparation of compound 4-4

Et₃N (0.285 mL, 1.46 mmol) was added to a stirred mixture of 4-3 (250 mg, 0.681 mmol) and phenyl 5-phenyl-1,3,4-thiadiazol-2-ylcarbamate (202 mg, 0.681 mmol) in CHCl₃ (3 mL), and the mixture was heated to reflux for 3 h. After being cooled to room temperature, the mixture was concentrated under reduced pressure. The residual oil was purified by silica gel column chromatography (10 g, hexane-EtOAc-MeOH 1:1:0→8:8:1) to give 4-4 (208 mg, 54%).

Step 4 Preparation of N-(5-phenyl-1,3,4-thiadiazol-2-yl)-1-sulfamoylspiro[indoline-3,4'-piperidine]-1'-carboxamide 400

To a stirred mixture of 4-4 in CHCl₃ (1 mL) was added TFA (1 mL). The mixture was stirred for 14 h and concentrated. The resulting mixture was diluted with EtOAc, washed with sat.NaHCO₃ and brine, dried (Na₂SO₄), and concentrated. The residual solid was crystallized from EtOAc and isopropyl ether to give compound 400 (130 mg, 76%) as colorless crystals.

m.p.: >300° C.

1H-NMR (DMSO-d6) was consistent with the proposed title structure.

FABMS: 471 (M+H)

Compounds #401 and #402 were prepared using the appropriate phenyl carbamates in analogy to the procedure of Example 4.

401

N-(4-phenyloxazol-2-yl)-1-sulfamoylspiro[indoline-3,4'-piperidine]-1'-carboxamide colorless amorphous solid.

1H-NMR (DMSO-d6) δ ppm: 1.59–1.69 (2 H, m), 1.71–1.85 (2 H, m), 2.95–3.10 (2 H, m), 3.81 (2 H, s), 4.05–4.17 (2 H, m), 6.98 (1 H, m), 7.17 (1 H, m), 7.18–7.48 (6 H, m), 7.68–7.75 (2 H, m), 8.33 (1 H, s).

402

N-(3-phenylisoxazol-5-yl)-1-sulfamoylspiro[indoline-3,4'-piperidine]-1'-carboxamide m.p.: 226–227° C.

EXAMPLE 5

1-Methanesulfamoyl-N-(5-phenyl-1,3,4-thiadiazol-2-yl)spiro[indoline-3,4'-piperidine]-1'-carboxamide 500

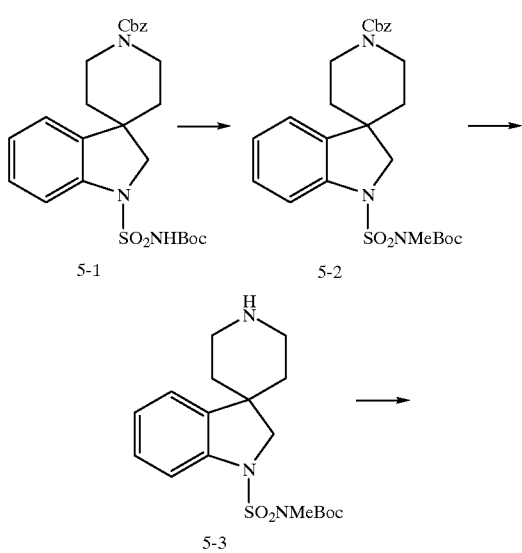

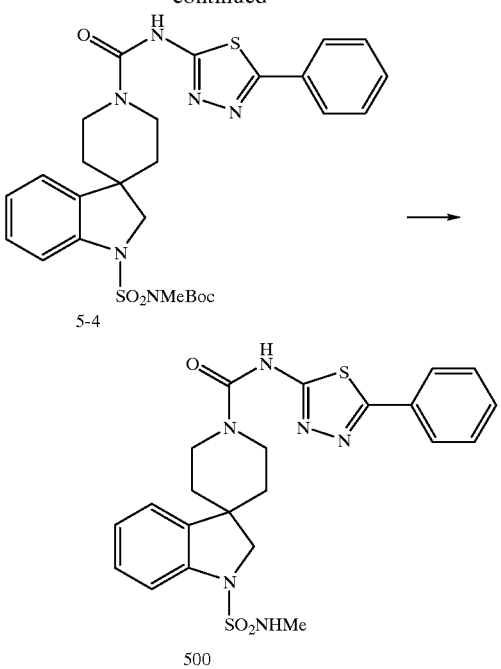

Step 1: Preparation of compound 5-2

To a stirred solution of 5-1 (542 mg, 1.08 mmol) and iodomethane (0.202 mL, 3.24 mmol) in DMF (3 mL) was added sodium hydride (contained 60% oil dispersion, 52 mg; 1.30 mmol) at 0° C. The mixture was stirred at room temperature for 2 h. The reaction mixture was poured into sat. NH₄Cl and extracted with EtOAc. The organic layer was washed with brine, dried (Na₂SO₄), and concentrated. The residual oil was purified by silica gel column chromatography (20 g, hexane-EtOAc 6:1→4:1) to give compound 5-2 (495 mg, 83%).

Step 2: Preparation of compound 5-3

A mixture of 450 mg (0.898 mmol) of 5-2 and 200 mg of 20% Pd(OH)₂—C in THF (5 mL) and MeOH (5 mL) was stirred under H₂ for 14 h. The catalyst was then filtered off and the filtrate was concentrated to give compound 5-3 (371 mg, 99%).

Step 3: Preparation of 1-methylsulfamoyl-N-(5-phenyl-1,3,4-thiadiazol -2-yl)spiro[indoline-3,4'-piperidine]-1'-carboxamide 500

To a stirred mixture of 5-3 (185 mg; 0.486 mmol) and phenyl 5-phenyl-1,3,4-thiadiazol-2-ylcarbamate (144 mg; 0.486 mmol) in CHCl₃ (2 mL) was added 0.285 mL (1.46 mmol) of Et₃N. The mixture was refluxed for 3 h and cooled to room temperature. Isopropyl ether was added to the mixture, and the resulting precipitate was collected by filtration to give crude product of 5-4. The crude product was dissolved in CHCl₃ (1 mL), and TFA (1 mL) was added. The mixture was stirred for 14 h and concentrated. The residue was dissolved in EtOAc, washed with sat.NaHCO₃ and brine, dried (Na₂SO₄), and concentrated. The residue was triturated with CHCl₃ to give 500 (130 mg, 55%) as a colorless solid.

m.p.: 230–231° C.

1H-NMR (DMSO-d6) was consistent with the proposed title structure.

FABMS: 485 (M+H)

EXAMPLE 6

1-Acetyl-N-(5-phenyl-1,3,4-thiadiazol-2-yl)spiro[indoline-3,4'-piperidine]-1'-carboxamide 600

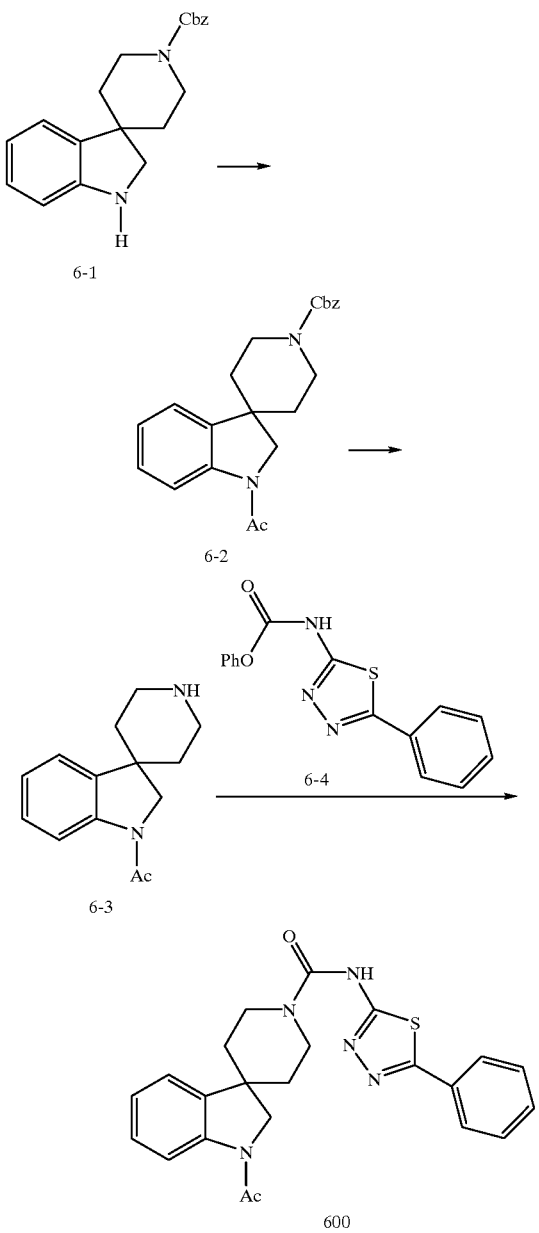

Step 1: Preparation of Compound 6-2

To a solution of 6-1 (267 mg, 0.87 mmol) in THF (5 mL), were added Et$_3$N (0.356 mL, 2.56 mmol) and AcCl (0.092 mL, 1.30 mmol). The resulting mixture was stirred at room temperature for 1 h. The mixture was diluted with ethyl acetate, washed with saturated NaHCO$_3$ and brine, dried (MgSO$_4$), and concentrated under reduced pressure. The residue was purified by silica gel column chromatography (n-hexane/ethyl acetate 2/1→1/1→1/2→1/4→1/8 (v/v)) to give 6-2 (260 mg, 82%).

Step 2 Preparation of Compound 6-3

To a solution of 6-2 (260 mg, 0.71 mmol) in EtOH/THF (6 mL/2 mL), was added 20% Pd(OH)$_2$—C (110 mg). The resulting mixture was stirred under H$_2$ at room temperature overnight. The catalyst was filtered off, and the filtrate was concentrated under reduced pressure to give 6-3 (155 mg, 91%).

Step 3: Preparation of Compound 600

To a solution of 6-3 (155 mg, 0.67 mmol) in CHCl$_3$ (3 mL), were added Et$_3$N (0.256 mL, 1.84 mmol) and phenyl 5-phenyl-1,3,4-thiadiazol-2-ylcarbamate 6-4 (182 mg, 0.61 mmol). The resulting mixture was stirred under reflux for 1.5 h. After being cooled to room temperature, the reaction mixture was diluted with CHCl$_3$, washed with saturated NaHCO$_3$ and brine. The organic layer was dried (MgSO$_4$) and concentrated under reduced pressure. The residue was triturated with Et$_2$O to give 600 (176 mg, 66%) as a white solid.

m.p.: 260° C.

1H-NMR (CDCl3) was consistent with the proposed title structure.

FABMS: 434 (M+H).

Employing the procedure substantially as described in Example 6, but substituting the appropriate phenyl carbamates, for the phenyl 5-phenyl-1,3,4-thiadiazol-2-ylcarbamate used in Step 3 thereof, the following compounds were prepared:

601
1-acetyl-N-(4-biphenyl)spiro[indoline-3,4'-piperidine]-1'-carboxamide

602
1-acetyl-N-(4-phenyloxazol-2-yl)spiro[indoline-3,4'-piperidine]-1'-carboxamide

603
1-acetyl-N-[3-(3-chlorophenyl)isoxazol -5-yl]spiro[indoline-3,4'-piperidine]1'-carboxamide

604
1-acetyl-N-[4-(3-pyridyl)phenyl]spiro[indoline-3,4'-piperidine]-1'-carboxamide

605
1-acetyl-N-[3-(4-chlorophenyl)pyrazol-5-yl]spiro[indoline-3,4'-piperidine]-1'-carboxamide

606
1-acetyl-N-(7-methoxybenzothiazol-2yl)spiro[indoline-3,4'piperidine]-1'-carboxamide

607
1-acetyl-N-(2-methylbenzothiazol-6-yl)spiro[indoline-3,4'-piperidine]-1'-carboxamide

608
1-acetyl-N-(quinolin-2-yl)spiro[indoline-3,4'-piperidine]-1'-carboxamide

609
1-acetyl-N-[3-(3-methoxyphenyl)-1-methylpyrazol-5-yl]spiro[indoline-3,4'-piperidine]-1'-carboxamide

610
1-acetyl-N-[3-(3-chlorophenyl)-1-methylpyrazol-5-yl]spiro[indoline-3,4'-piperidine]-1'-carboxamide

611
1-acetyl-N-(5-phenyl-1,2,4-thiadiazol-3-yl)spiro[indoline-3,4'piperidine]-1'-carboxamide

612
1-acetyl-N-(3-phenylpyrazol-5-yl)spiro[indoline-3,4'-piperidine]-1'-carboxamide

613
1-acetyl-N-(2-phenylpyrazin-5-yl)spiro[indoline-3,4'-piperidine]-1'-carboxamide

614
1-acetyl-N-(3-phenylpyridazin-6-yl)spiro[indoline-3,4'-piperidine]-1'-carboxamide

615
1-acetyl-N-(5-phenylpyrimidin-2-yl)spiro[indoline-3,4'-piperidine]-1'-carboxamide

616
1-acetyl-N-(2-phenylpyrimidin-5-yl)spiro[indoline-3,4'-piperidine]-1'-carboxamide

EXAMPLE 7

1-Formyl-N-(5-phenyl-1,3,4-thiadiazol-2-yl)spiro[indoline-3,4'-piperidine]-1'-carboxamide 700

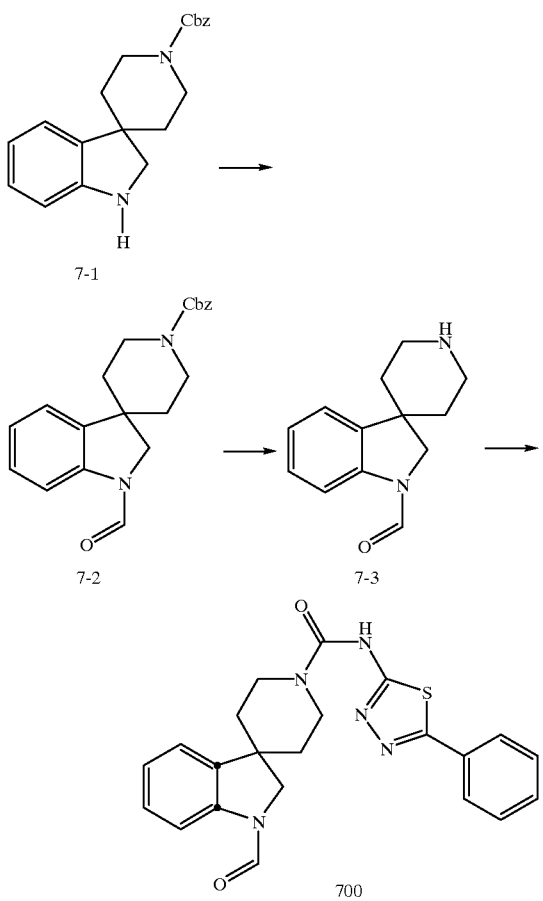

7-1

7-2　　7-3

700

Step 1: Preparation of Compound 7-2

A mixture of 7-1 (300 mg, 3.54 mmol) and p-TsOH.H$_2$O (10 mg) in ethyl formate (5 mL) was stirred under reflux for 20 hr. After being cooled to room temperature, the reaction mixture was concentrated under reduced pressure. The residue was taken up with CHCl$_3$, which was washed with saturated NaHCO$_3$ and brine. The organic layer was dried (MgSO$_4$) and concentrated under reduced pressure. The residue was purified by silica gel column chromatography (n-hexane/ethyl acetate 4/1→1/1 (v/v)) to give 7-2 (290 mg, 89%).

Step 2: Preparation of Compound 7-3

To a solution of 7-2 (290 mg, 0.83 mmol) in EtOH/THF (7 mL/5 mL) was added 20% Pd(OH)$_2$—C (360 mg). The resulting mixture was stirred under H$_2$ at room temperature overnight. The catalyst was filtrated off, and the filtrate was concentrated under reduced pressure to give 7-3 (160 mg, 89%).

Step 3: Preparation of Compound 700

Compound 7-3 (320 mg, 1.48 mmol) was dissolved in CHCl$_3$ (5 mL), and Et$_3$N (0.560 mL, 4.02 mmol) and phenyl 5-phenyl-1,3,4-thiadiazol-2-ylcarbamate (400 mg, 1.34 mmol) were added. The resulting mixture was stirred under reflux for 1 h. The reaction mixture was cooled to room temperature and diluted with CHCl$_3$, which was washed with saturated NaHCO$_3$ and brine. The organic layer was dried (MgSO$_4$) and concentrated under reduced pressure. The residue was purified by silica gel column chromatography (n-hexane/ethyl acetate/methanol 10/1/0→6/1/0→1/1/0→6/6/1→3/3/1→1/1/1(v/v/v)) to give 7-4 (200 mg, 72%) as a white amorphous solid.

1H-NMR (CDCl3) was consistent with the proposed title structure.

FABMS: 420 (M+H)

EXAMPLE 8

1-Dimethylcarbamoyl-N-(5-phenyl-1,3,4-thiadiazol-2-yl)spiro[indoline-3,4'-piperidine]-1'-carboxamide 800

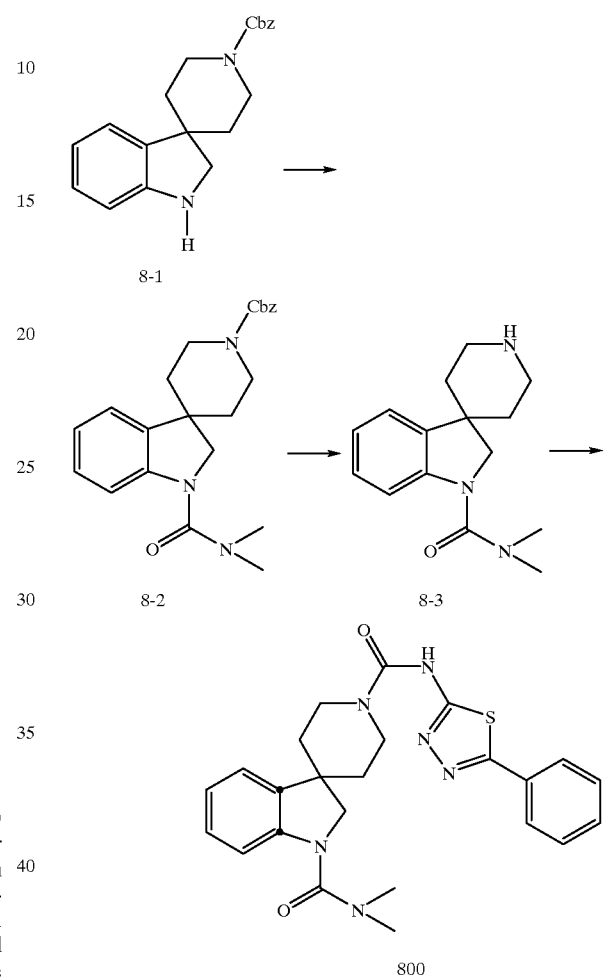

8-1

8-2　　8-3

800

Step 1: Preparation of Compound 8-2

To a solution of 8-1 (400 mg, 1.30 mmol) in DMF (3 mL), was added NaH (62 mg, 2.60 mmol, washed with dry n-hexane before use), and the mixture was stirred at room temperature for 30 min. Dimethyl carbamoyl chloride (0.18 mL, 1.95 mmol) was added to the mixture, and the reaction mixture was stirred at room temperature for 24 h. The mixture was diluted with ethyl acetate, washed with saturated NaHCO$_3$ and brine, dried (MgSO$_4$), and concentrated under reduced pressure. The residue was purified by silica gel column chromatography (n-hexane/ethyl acetate 1/1→1/2→1/4 (v/v)) to give 8-2 (535 mg) as a crude product.

Step 2 Preparation of Compound 8-3

To a solution of 8-2 (535 mg, 1.36 mmol) in EtOH/THF (3 mL/1 mL) was added 20% Pd(OH)$_2$—C(200 mg). The resulting mixture was stirred under H$_2$ at room temperature overnight. The catalyst was filtrated off, and the filtrate was concentrated under reduced pressure to give 8-3 (320 mg, 95%, two steps).

Step 3: Preparation of Compound 800

Compound 8-3 (300 mg, 1.16 mmol) was dissolved in CHCl$_3$ (3 mL), and Et$_3$N (0.44 ml, 3.15 mmol) and phenyl 5-phenyl-1,3,4-thiadiazol-2-ylcarbamate (317 mg, 1.05 mmol) were added. The resulting mixture was stirred under reflux overnight. The reaction mixture was cooled to room temperature and extracted with CHCl$_3$, which was washed with a saturated NaHCO$_3$ and brine. The organic layer was dried (MgSO$_4$) and concentrated under reduced pressure. The residue was triturated with Et$_2$O to give 800 (334 mg, 69%) as a white solid.

m.p.: 267° C.

1H-NMR (CDCl3) was consistent with the proposed title structure.

FABMS: 463 (M+H)

Compounds, in which X is carbon atom and Z is nitrogen atom in the following general formula, are generally prepared according to Example 9.

EXAMPLE 9

1-Acetyl-N-(3-quinolinyl)spiro[indoline-3,4'-cyclohexane]-1'-carboxamide 900

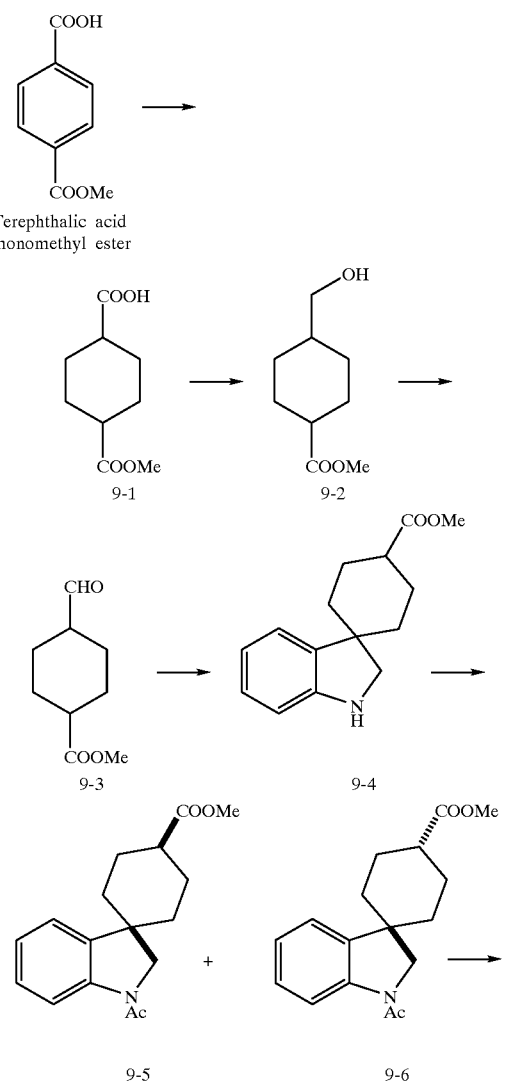

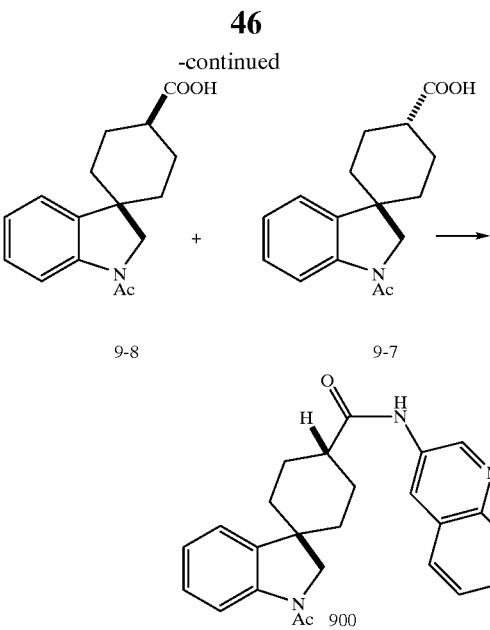

Step 1: Preparation of Compound 9-1

A mixture of terephthalic acid monomethylester (40.0 g, 0.222 mol) and 5% Rh—C (wet)(40 g) in 1,4-dioxane (200 mL) and MeOH (160 mL)was stirred under H$_2$ at 50 atm for 18 h. The catalyst was then filtered off and the filtrate was concentrated to give 41.0 g (99%) of 9-1.

Step 2: Preparation of Compound 9-2

To a stirred solution of 41.0 g (0.220 mol) of 9-1 in THF (200 mL) cooled at 0° C. was added 27.4 mL (0.289 mol) of Me$_2$S.BH$_3$. The solution was stirred at room temperature for 3 h and AcOH (6 mL) was added. The resulting mixture was diluted with H$_2$O and extracted with EtOAc. The organic layer was washed with brine, dried (Na$_2$SO$_4$), and concentrated to give 36.1 g (95%) of 9-2.

Step 3: Preparation of Compound 9-3

To a stirred mixture of Celite (10 g) and 9-2 (3.00 g; 17.4 mmol) in CH$_2$Cl$_2$(60 mL) was added PCC (11.3 g; 52.3 mmol). The mixture was stirred at room temperature for 3 h and diluted with hexane (100 mL). The resulting mixture was then filtered and the filtrate was concentrated to give 9-3 (2.65 g; 90%).

Step 4: Preparation of Compound 9-4

To a stirred solution of 9-3 (2.65 g; 15.6 mmol) in 35 mL of PhMe—MeCN (39:1) cooled at 0° C. were added phenylhydrazine (1.54 mL; 15.6 mmol) and TFA (3.61 mL; 46.8 mmol). The mixture was stirred at room temperature for 16 h and MeOH (35 mL) was added. The mixture was cooled to 0° C. and NaBH$_4$(885 mg; 23.4 mmol) was added and stirred at 0° C. for 1 h. The reaction mixture was poured into sat. NaHCO$_3$ and extracted with EtOAc. The organic layer was washed with H$_2$O and brine, dried (Na$_2$SO$_4$), and concentrated to give the crude product 9-4 (3.60 g).

Step 5: Preparation of Compound 9-5 and 9-6

To a stirred solution of crude product 9-4 in THF (50 mL) cooled at 0° C. were added Et$_3$N (6.52 mL; 46.8 mmol) and AcCl. (2.22 mL; 31.2 mmol). The mixture was stirred at 0° C. for 1 h then poured into 10% citric acid. The resulting mixture was extracted with EtOAc. The organic layer was washed with sat. NaHCO$_3$ and brine, dried (Na$_2$SO$_4$), and concentrated. The residual oil was purified by silica gel column chromatography (100 g, hexane-EtOAc 3:1→2:1→4:3) to give 577 mg of 9-5 (14%) and 1.42 g of the mixture of 9-5 and 9-6 (33%).

Step 6: Preparation of Compound 9-7 and 9-8

To a stirred solution of 9-6 (1.42 g; 5.20 mmol) in MeOH (20 mL) was added 4N NaOH (5.2 mL; 20.8 mmol). The solution was stirred at room temperature for 3 h and the MeOH was concentrated. 1N HCl (30 mL) was added and extracted with EtOAc. The organic layer was washed with brine, dried ($Na_2SO_4$), and concentrated. The residual oil was purified by silica gel column chromatography (80 g, $CHCl_3$-MeOH 1:0 200:1 100:1) to give 367 mg of 9-7 (26%) and 627 mg of 9-8 (44%).

Step 7: Preparation of Compound 900

To a stirred solution of 20 mg (73.3 mmol) of 9-7 (20 mg; 73.3 mmol) and 3-aminoquinoline (21 mg; 73.3 mmol) in pyridine (0.5 mL) was added WSC.HC (21 mg; 101 mmol). The mixture was stirred at 50° C. for 1 h. The reaction mixture was poured into $H_2O$ and extracted with EtOAc. The organic layer was washed with $H_2O$ and brine, dried ($Na_2SO_4$), and concentrated. The residual oil was purified by silica gel column chromatography (5 g, hexane-EtOAc-MeOH 1:1:0→8:8:1→6:6:1→4:4:1) to give 300 (17.0 mg; 58%) as a colorless amorphous solid.

1H-NMR (DMSO-d6) was consistent with the proposed title structure.

FABMS: 400 (M+H)

The following compounds #901–#905 were prepared from the appropriate amines in analogy to the procedure of Example 9.

901
trans-N-(4-biphenylyl)-1-methylsulfonylspiro[indoline-3,4'-cyclohexane]-1'-carboxamide
m.p.: 119.8–120.5° C.

902
trans-1-methylsulfonyl-N-[4-(3-pyridyl)phenyl]spiro[indoline-3,4'-cyclohexane]-1'-carboxamide
m.p.: 212.5–213.0° C.

903
trans-1-methylsulfonyl-N-(5-phenylpyrrazol-3-yl)spiro[indoline-3,4'-cyclohexane]-1'-carboxamide
m.p.: 212–213° C.

904
trans-N-[1-(3,5-difluorophenyl)imidazol-4-yl]-1-methylsulfonylspiro[indoline-3,4'-cyclohexane]-1'-carboxamide
m.p.: 287–292° C.

905
trans-N-[1-(4-fluorophenyl)imidazol-4-yl]-1-methylsulfonylspiro[indoline-3,4'-cyclohexane]-1'-carboxamide
m.p.: 264–266° C.

EXAMPLE 10

2,3-Dihydro-1-methanesulfonyl-N-(5-phenyl-pyrazinyl)spiro[1H-indene-3,4'-piperidine]-1'-carboxamide 1000

Step 1: Preparation of Compounds 10-2 and 10-3

Indene 10-1 was synthesized by the method described in U.S. Pat. No. 5,536,716

To a solution of indene 10-1 (9.82 g, 34.4 mmol) in THF (100 mL) was slowly added 2M $BH_3.SMe_2$ in THF (24.1 mL, 48.2 mmol) at 0°. After being stirred for 4 h at 0°, the mixture was treated with 2 N NaOH (100 mL) and 30% $H_2O_2$ (25 mL) for 30 min at 0°. The organic layer was separated and the aqueous layer was extracted with ether (100 mL×2). The combined organic layer was washed with 5% $Na_2S_2O_3$ aqueous and brine, dried ($Na_2SO_4$), and was evaporated off. The residue was purified by silica gel column chromatography hexane/ethyl acetate (600 mL 4/1→2/1) to give 10-2 (4.83 g, 46%) as an amorphous solid and its regioisomer 10-3 (5.02 g, 48%) as a solid.

Step 2: Preparation of Compound 10-4

To a solution of alcohol 10-2 (4.83 g, 15.9 mmol) in $CHCl_3$ (70 mL) and triethylamine (6.65 mL) was slowly added methanesulfonyl chloride (2.46 mL) at 0°. The mixture was stirred for 15 min and was diluted with $Et_2O$. The organic layer was washed with aqueous $NH_4Cl$, saturated aqueous $NaHCO_3$ and brine, dried ($Na_2SO_4$) and concentrated in vacuo.

The residue was dissolved in DMF (40 mL) and sodium thiomethoxide (2.23 g, 31.8 mmol) was added to the solution. After being stirred for 50 min at room temperature, the resulting mixture was poured into water, and extracted with $Et_2O$, and washed with water and brine. The organic layer was dried ($Na_2SO_4$) and concentrated in vacuo.

The residue was dissolved with $CHCl_3$ (100 mL) and MCPBA (10.3 g, 47.7 mmol) was added to the solution at 0°. After being stirred for 20 min at 0°, to the suspension was added aqueous $Na_2S_2O_3$ and aqueous $NaHCO_3$. The mixture was extracted with $Et_2O$, and washed with saturated $NaHCO_3$ aqueous twice and brine. The organic layer was dried ($MgSO_4$), and concentrated in vacuo. The residue was purified by silica gel chromatography (Merck 7734, 300 mL, Hexane/ethyl acetate=1/1) to give 5.33 g (92%) of sulfone 10-4.

Step 3: Preparation of Compound 10-5

Sulfone 10-4 (5.27 g) was dissolved in ethyl acetate (50 mL) and the solution was treated with 4N HCl in ethyl acetate (10 mL) at 0°. After being stirred for 2.5 hr. at room temperature, to the mixture was again added 4N HCl in ethyl acetate (10 mL). After being stirred for 2.5 h, the resulting mixture was evaporated and the residue was suspended in ethyl acetate and collected to give amine HCl salt 10-5 (3.72 g; 85%) as a white solid.

Step 4: Preparation of Compound 1000

Amine HCl salt 10-5 (160 mg) and phenoxy compound 10-6 (153 mg, 0.53 mmol) were suspended in $CHCl_3$ (3.0 mL) and triethylamine (0.16 mL), and the suspension was refluxed for 3 h. The resulting mixture was cooled to room temperature. After diluting with ethyl acetate, the organic layer was washed with $NH_4Cl$ aqueous, saturated aqueous $NaHCO_3$ and brine. The organic layer was dried ($Na_2SO_4$) and concentrated in vacuo. The residue was suspended with ethyl acetate and IPE, and collected to give urea 1000 (177 mg) as a solid.

The following compounds were prepared by the procedures deesdcribed in Example 10 procedure of Example 10.

1001

2,3-dihydro-1-methylsulfonyl-N-(4-phenyl-2-oxazolyl)spiro[1H-indene-3,4'-piperidine]-1'-carboxamide amorphous solid.

1H-NMR (CDCl3) δ ppm: 1.79–1.87 (2 H, m), 2.00–2.10 (2 H, m), 2.42 (1 H, dd, J=14.5 Hz, 6.5 Hz), 2.75(1 H, dd, J=14.5 Hz, 9.6 Hz), 2.80 (3 H, s), 2.99–3.09 (2 H, m), 4.56–4.61 (2 H, m), 4.72 (1 H, dd, J=9.6 Hz, 6.5 Hz), 7.21–7.49 (10 H, m), 7.69 (1 H, d, J=7.6 Hz).

1002

2,3-dihydro-1methylsulfonyl-N-[3-(3-chlorophenyl)-5-isoxazolyl)spiro[1H-indene-3,4'-piperidine]-1'-carboxamide amorphous solid.

1H-NMR ((CD3)2CO) δ ppm: 1.89–7.06 (4 H, m), 2.74 (1 H, dd, J=14.3 Hz, 6.2 Hz), 2.79 (1 H, dd, J=14.3 Hz, 9.3 Hz), 2.96 (3 H, s), 3.20–3.23 (2 H, m), 4.30–4.35 (2 H, m), 4.94 (1 H, dd, J=9.3 Hz, 6.2 Hz), 6.63 (1H, s), 7.29–7.34 (1 H, m), 7.38–7.40 (2 H, m), 7.52–7.54 (2 H, m), 7.66 (1 H, d, J=7.5 Hz), 7.81–7.84 (1 H, m), 7.89 (1 H, d, J=1.2 Hz), 9.50 (1 H, s).

EXAMPLE 11

2,3-Dihydro-1-methyl thio-N-4-biphenylylspiro[1H-indene-3,4'-piperidine]-1-carboxamide 1100

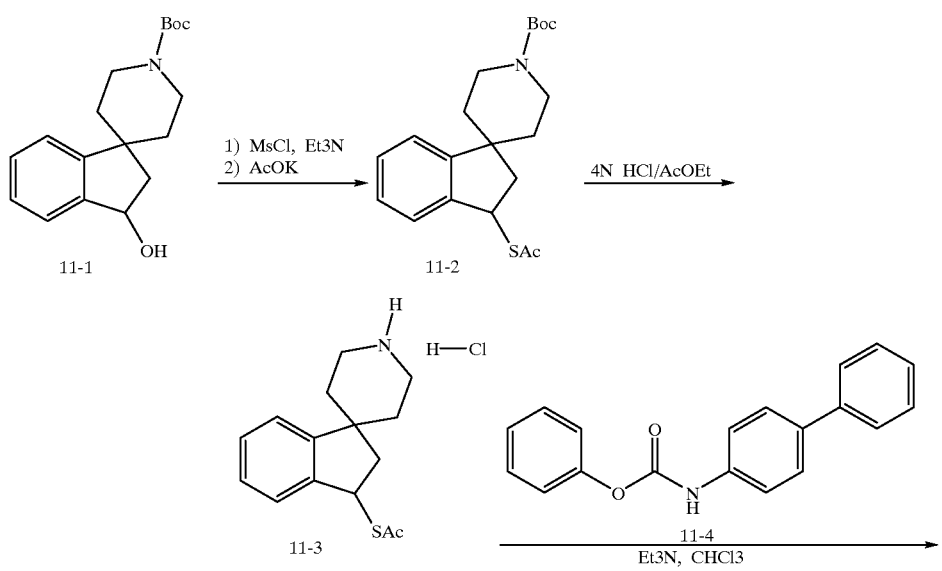

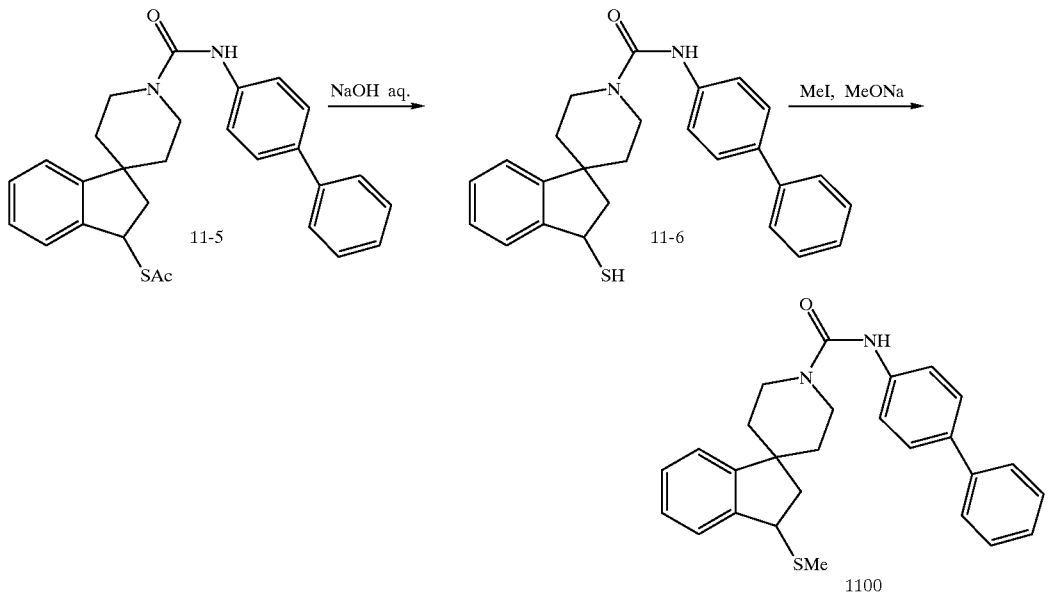

Step 1: Preparation of Compound 11-2

To a solution of alcohol 11-1 (1.05 g, 3.46 mmol) in CHCl$_3$ (15 mL) and triethylamine (1.45 mL, 10.4 mmol) was added methanesulfonyl chloride (0.535 mL, 6.92 mmol) at 0°. The mixture was stirred for 15 min and was diluted with Et$_2$O. The organic layer was washed with NH$_4$Cl aqueous, aqueous saturated NaHCO$_3$ and brine, dried (Na$_2$SO$_4$) and concentrated in vacuo. The residue was dissolved in DMSO (15 mL) and potassium thioacetate (395 mg, 31.1 mmol) was added to the solution. After being stirred for 1.5 h at room temperature, the resulting mixture was poured into water and extracted with Et$_2$O. The organic layer was washed with water and brine, dried (Na$_2$SO$_4$), and concentrated in vacuo. The residue was purified by a silicagel chromatography (WAKO C-200, Hexane/ethyl acetate=8/1→5/1) to give thioacetate 11-2 (1.05 g; 89%).

Step 2: Preparation of Compound 11-3

Thioacetate 11-2 (222 mg, 0.614 mmol) was dissolved in ethyl acetate (2.0 mL) and the solution was treated with 4N HCl in ethyl acetate (5.0 mL). After being stirred for 3.5 h. at room temperature, the resulting mixture was evaporated and the residue was co-evaporated three times with CHCl$_3$, was diluted and collected to give amine HCl salt 11-3 (201 mg, quant.) as an amorphous solid.

Step 3: Preparation of Compound 11-5

Amine HCl salt 11-3 (201 mg, 0.614 mmol) and phenoxy compound 11-4 (176 mg; 0.608 mmol) were suspended in CHCl$_3$ (6.0 mL) and triethylamine (0.200 mL), and the suspension was refluxed for 3 h. The resulting mixture was cooled to room temperature. After diluting with ethyl acetate, the organic layer was washed with aqueous NH$_4$Cl, saturated aqueous NaHCO$_3$ and brine. The organic layer was dried over Na$_2$SO$_4$ and concentrated in vacuo. The residue was suspended with ethanol and collected to give urea 11-5 (235 mg; 84%) as a solid.

Step 4: Preparation of Compound 11-6

Urea 11-5 (200 mg) was dissolved in methanol (3.0 mL) and THF (3.0 mL) and the solution was treated with 2N NaOH aqueous (3.0 mL) at 60° for 1.5 h. The resulting mixture was poured into water and extracted with ethyl acetate, and washed with brine. The organic layer was dried (Na$_2$SO$_4$) and concentrated in vacuo. The residue was suspended with ethyl acetate and hexane, and collected to give thiol 11-6 (155 mg; 85%) as a white solid.

Step 5: Preparation of Compound 1100

To the solution of thiol 11-6 (79.5 mg,) in anhydrous methanol (3.0 mL) was added sodium methoxide (31.1 mg) and methyl iodide (0.036 mL). After being stirred for 12 h at room temperature, the resulting mixture was diluted with ethyl acetate and washed with water and brine. The organic layer was dried (Na$_2$SO$_4$) and concentrated in vacuo. The residue was triturated with IPE to give methylthio compound 1100 (72.6 mg; 88%) as a white solid.

EXAMPLE 12

2,3-Dihydro-1-methylsulfinyl-N-4-biphenylylspiro[1H-indene-3,4'-piperidine]-1'-carboxamide 1200

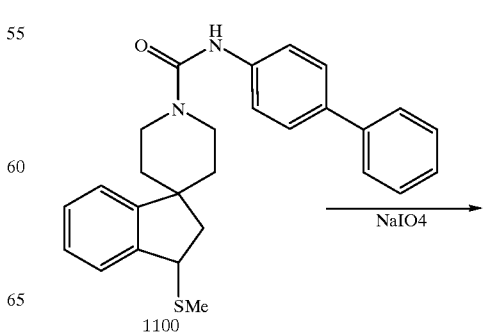

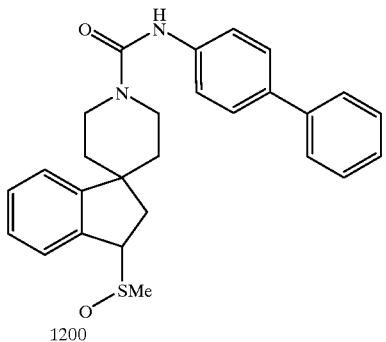

1200

To a solution of 2,3-dihydro-1methylthio-N-4-biphenylyspiro[1H-indene-3,4'-piperidine]-1'-carboxamide, (1100, 55.4 mg, 0.129 mmol) in methanol (3.0 mL), THF (2.0 mL) and H₂O (1.0 mL) was added sodium meta periodade (34.6 mg, 0.161 mmol). After being stirred for 35 h at room temperature, the resulting mixture was diluted with water and extracted with ethyl acetate. The organic layer was washed with water and brine, dried (Na₂SO₄), and concentrated in vacuo. The residue was triturated with ethyl acetate and isopropyl ether to give 2,3-dihydro-1-methylsulfinyl-N-4-biphenylylspiro[1H-indene-3,4'-piperidine]-1'-carboxamide 45.4 mg; 79%) as an amorphous solid, 1200.

1H-NMR (CDCl3) δ ppm: 1.90–2.10 (4 H, m), 2.30–2.50 (1 H, m), 2.50–2.70 (0.5 H, m), 2.48 (1.5 H, s), 2.55 (1.5 H, s), 2.73–2.82 (0.5 H, m), 3.05–3.30 (2 H, m), 4.00–4.30 (2 H+0.5 H, m), 4.39–4.47 (0.5 H, m), 6.55–6.67 (0.5 H, brs), 6.67–6.80 (0.5 H, brs), 7.20–7.60 (13 H, m).

FABMS: 446 (M+H)

EXAMPLE 13

4-aza-1-methylsulfonyl-N-(5-phenyl-2-pyrazinyl)spiro[indoline-3,4'-piperidine]-1'-carboxamide hydrochloride, 1300

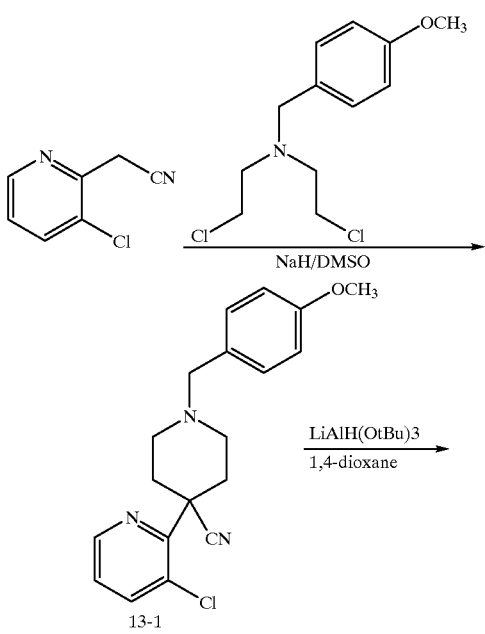

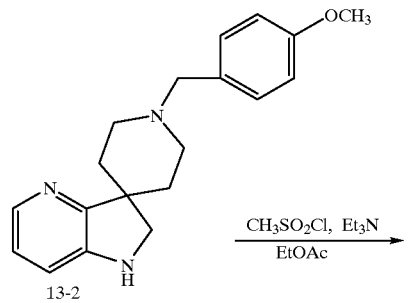

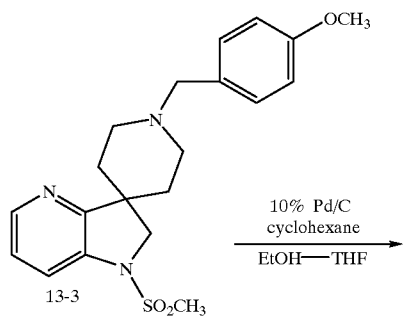

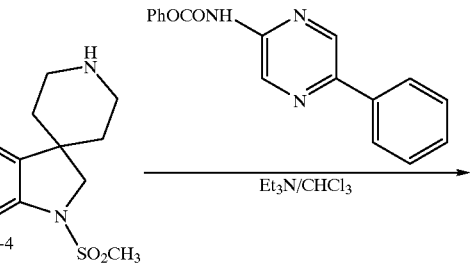

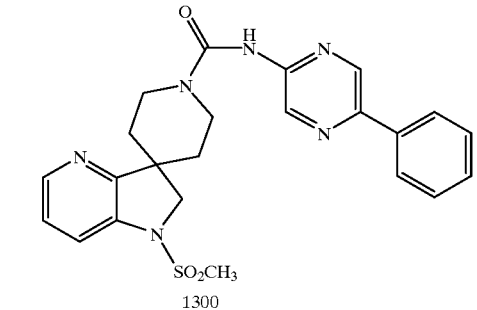

1300

Step 1. Preparation of 4-(3-chloro-2-pyridyl)-4-cyano-1-(4-methoxyphenyl)methylpiperidine (13-1)

A solution of 3-chloro-2-pyridylacetonitrile [prepared by the method described in JP08295663] (1.46 g, 9.57 mmol) in DMSO (19 mL) was slowly added to NaH (60% oil dispersion, 1.01 g, 25.3 mmol), and the mixture was stirred at room temperature for 1 h. A solution of N,N-bis(2-chloroethyl)-p-methoxybenzylamine (2.21 g, 8.43 mmol) in DMSO (19 ml,) was added, and the resulting mixture was stirred at 75° C. for 4 h. After cooling, water (100 mL) was added, and the mixture was extracted with ethyl acetate. The organic extract was washed with brine, dried (Na₂SO₄), and the solvent was removed under reduced pressure. The residue was purified by silica gel column chromatography (hexane/ethyl acetate=3/2) to give 4-(3-chloro-2-pyridyl)-4-cyano-1-(4-methoxyphenyl)methylpiperidine 1 (1.91 g, 60%) as an orange oil.

Step 2. Preparation of 4-aza-1'-(4-methoxyphenyl)methylspiro[indoline-3,4'-piperidine] (13-2)

A mixture of 4-(3-chloro-2-pyridyl)-4-cyano-1-(4-methoxyphenyl)methylpiperidine (1.91 g, 5.59 mmol) and lithium tri-tert-butoxyaluminohydride (1 M solution in THF, 22 mL) in 1,4-dioxane (28 mL) was stirred at 125° C. overnight in a sealed tube. After cooling, 1 N aqueous NaOH solution (50 mL) and ethyl acetate were added to the mixture, and the mixture was filtered through Celite. The organic layer was separated and washed with brine, dried (NaSO4), and concentrated under reduced pressure. The residue was purified by silica gel column chromatography (hexane/ethyl acetate=7/3→chloroform/methanol=9/1) to give 4-aza-1'-(4-methoxyphenyl)methylspiro[indoline-3,4'-piperidine] (2) (0.80 g, 46%) as an orange solid.

Step 3. Preparation of 4-aza-1'-(4-methoxyphenyl)methyl-1-methylsulfonylspiro[indoline-3,4'-piperidine] (13-3)

To a suspension of 4-aza-1'-(4-methoxyphenyl)methylspiro[indoline-3,4'-piperidine] (0.80 g, 2.59 mmol) in ethyl acetate (13 mL) were added Et₃N (1.08 mL, 7.77 mmol) and methylsulfonyl chloride (0.24 mL, 3.1 mmol) at 0° C., and the mixture was stirred at the same temperature for 1.5 h. The mixture was diluted with ethyl acetate, washed with brine and dried (NaSO4). The solvent was evaporated in vacuo, and the residue was purified by silica gel column chromatography (chloroform/methanol=99/1) to give 4-aza-1'-(4-methoxyphenyl)methyl-1-methylsulfonylspiro[indoline-3,4'-piperidine] (476 mg, 47%).

Step 4. Preparation of 4-aza-1-methylsulfonylspiro[indoline-3,4'-piperidine] (13-4)

A mixture of 4-aza-1'-(4-methoxyphenyl)methyl-1-methylsulfonylspiro[indoline-3,4'-piperidine] (476 mg, 1.23 mmol), cyclohexene (3 mL) and 10% Pd/C (500 mg) in ethanol (12 mL) and THF (12 mL) was refluxed for 5 h. The catalyst was removed by filtration, and the filtrate was concentrated under reduced pressure. Purification of the residue by column chromatography on alumina (chloroform/methanol=9/1) gave 4-aza-1-methylsulfonylspiro[indoline-3,4'-piperidine] (102 mg, 31%).

Step 5. Preparation of 4-aza-1-methylsulfonyl-N-(5-phenyl-2-pyrazinyl)spiro[indoline-3,4'-piperidine]-1'-carboxamide hydrochloride 1300

A mixture of 4-aza-1-methylsulfonylspiro[indoline-3,4'-piperidine] (100 mg, 0.37 mmol), phenyl N-(5-phenyl-2-pyrazinyl)carbamate (108 mg, 0.37 mmol) and Et3N (0.26 mL, 1.87 mmol) in CHCl3 (1.9 mL) was refluxed for 1.5 h. After cooling, the mixture was diluted with EtOAc, washed with aqueous saturated NaHCO3 and brine, dried over MgSO4, and concentrated under reduced pressure. The residue was dissolved in chloroform, and 4 N HCl/ethyl acetate (0.38 mL) was added. The solvent was evaporated, and the residue was crystallized from methanol, chloroform and diisopropyl ether to give 4-aza-1-methylsulfonyl-N-(5-phenyl-2-pyrazinyl)spiro[indoline-3,4'-piperidine]-1'-carboxamide hydrochloride (143 mg, 76%) as a brown powder.

m.p.: 138–145° C.

1H-NMR (CDCl3) was consistent with the proposed title structure.

FABMS: 465 (M+H)

EXAMPLE 14

7-aza-1-methylsulfonyl-N-(5-phenyl-2-pyrazinyl)spiro[indoline-3,4'-piperidine]-1'-carboxamide, (1400)

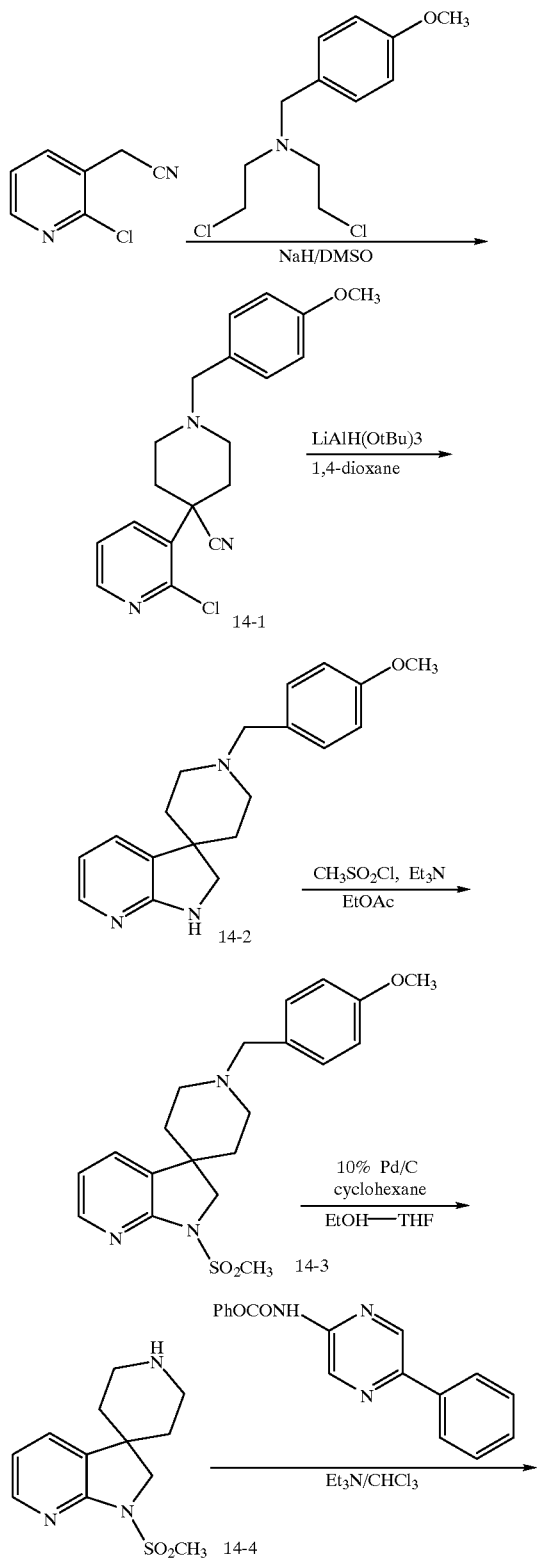

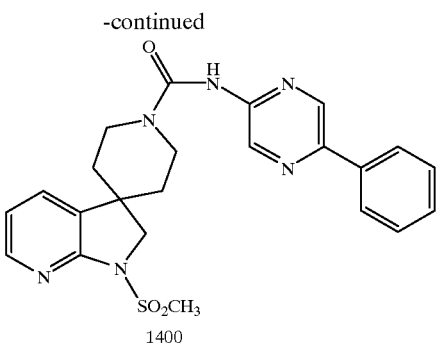

1400

Step 1. Preparation of 4-(3-chloro-2-pyridyl)-4-cyano-1-(4-methoxyphenyl)methylpiperidine (14-1)

A solution of 2-chloro-3-pyridylacetonitrile [prepared by the method of Bremner, et al, Synthesis, 1992, 6, 528–530] (2.14 g, 14.0 mmol) in DMSO (28 mL) was slowly added to NaH (60% in oil, 1.51 g, 37.8 mmol), and the mixture was stirred at room temperature for 1 h. A solution of N,N-bis (2-chloroethyl)-p-methoxybenzylamine (3.67 g, 14.0 mmol) in DMSO (28 mL) was added, and the resulting mixture was stirred at 75° C. for 4 h. After cooling, the mixture was partitioned between water and ethyl acetate, and the aqueous layer was extracted with ethyl acetate. The combined organic layers were washed with 1 N aqueous NaOH solution and brine, dried over $Na_2SO_4$, and concentrated under reduced pressure. The residue was purified by silica gel column chromatography (hexane/ethyl acetate 9/1→1/1) to give 4-(2-chloro-3-pyridyl)-4-cyano-1-(4-methoxyphenyl) methylpiperidine 1 (1.62 g, 34%) as a brown solid.

Step 2. Preparation of 7-aza-1'-(4-methoxyphenyl) methylspiro[indoline-3,4'-piperidine] (14-2)

A mixture of 4-(2-chloro-3-pyridyl)-4-cyano-1-(4-methoxyphenyl)methylpiperidine (1.62 g, 4.74 mmol) and lithium tri-tert-butoxyaluminohydride (1 M solution in THF, 19 mL) in 1,4-dioxane (24 mL) was stirred at 130° C. overnight in a sealed tube. After cooling, 1 N NaOH (50 mL) and EtOAc were added to the mixture, and the mixture was filtered through Celite. The organic layer was separated and washed with brine, dried ($Na_2SO_4$), and concentrated under reduced pressure. The residue was purified by silica gel column chromatography (hexane/ethyl acetate 4/1→chloroform/methanol 9/1) to give 7-aza-1'-(4-methoxyphenyl)methylspiro[indoline-3,4'-piperidine] (2) (0.96 g, 66%) as a brown solid.

Step 3. Preparation of 7-aza-1'-(4-methoxyphenyl)methyl-1-methylsulfonylspiro[indoline-3,4'-piperidine] (14-3)

To a suspension of 7-aza-1'-(4-methoxyphenyl) methylspiro[indoline-3,4'-piperidine] (0.96 g, 3.10 mmol) in EtOAc (16 mL) were added $Et_3N$ (1.30 mL, 9.30 mmol) and methylsulfonyl chloride (0.36 mL, 4.65 mmol) at 0° C., and the mixture was stirred at the same temperature for 2 h. The mixture was diluted with EtOAc, washed with brine and dried ($Na_2SO_4$). The solution was passed through a pad of silica gel and the pad was washed with ethyl acetate. The filtrate and washing were combined, and the solvent was evaporated to give 7-aza-1'-(4-methoxyphenyl) methyl-1-methylsulfonylspiro[indoline-3,4'-piperidine] (0.99 g, 82%) as a brown amorphous solid.

Step 4. Preparation of 7-aza-1-methylsulfonylspiro [indoline-3,4'-piperidine] (14-4)

A mixture of 7-aza-1'-(4-methoxyphenyl)methyl-1-methylsulfonylspiro[indoline-3,4'-piperidine] (0.82 g, 2.12 mmol), cyclohexene (5 mL) and 10% Pd/C (0.82 g) in EtOH (20 mL) and THF (20 mL) was refluxed for 2 h. The catalyst was removed by filtration, and the filtrate was concentrated under reduced pressure. The residue was reprecipitated from MeOH, EtOAc and IPE to give 7-aza-1-methylsulfonylspiro [indoline-3,4'-piperidine] (0.47 g, 83%) as a brown powder.

Step 5. Preparation of 7-aza-1-methylsulfonyl-N-(5-phenyl-2-pyrazinyl)spiro[indoline-3,4'-piperidine]-1'-carboxamide, 1400

A mixture of 7-aza-1-methylsulfonylspiro[indoline-3,4'-piperidine] (134 mg, 0.50 mmol), phenyl N-(5-phenyl-2-pyrazinyl)carbamate (116 mg, 0.45 mmol) and Et3N (0.35 mL, 2.5 mmol) in CHCl3 (2.5 mL) was stirred at 90° C. in a sealed tube for 1.5 h. After cooling, the mixture was diluted with EtOAc, washed with NaHCO3 and brine, dried (Na2SO4), and concentrated under reduced pressure. Purification of the residue by column chromatography on silica gel (hexane/ethyl acetate=7/3→chloroform/methanol=9/1) gave 7-aza-1-methylsulfonyl-N-(5-phenyl-2-pyrazinyl) spiro[indoline-3,4'-piperidine]-1'-carboxamide (181 mg, 78%) as a white powder.

m.p.: 214–215° C.

1H-NMR (CDCl3) was consistent with the proposed title structure.

FABMS: 465 (M+H)

Compound #1401 and #1402 were prepared from 7-aza-1-methylsulfonylspiro[indoline-3,4'-piperidine] and phenyl N-(4-benzoylphenyl)carbamate or phenyl N-(3-phenyl-5-isoxazolyl)carbamate, respectively, according to the procedure described in Example 14.

1401

7-aza-N-(4-benzoylphenyl)-1-methylsulfonylspiro [indoline-3,4'-piperidine]-1'-carboxamide pale yellow amorphous solid.

1H-NMR (DMSO-d6) δ ppm: 1.69–1.90 (4 H, m),3.02–3.12 (2 H, m), 3.29 (3 H, s), 3.97 (2 H, s), 4.05–4.20 (2 H, m), 7.00 (1 H, dd, J=7.5, 5.0 Hz), 7.50–7.80 (10 H, m), 8.12 (1 H, dd, J=5.0, 1.4 Hz), 9.0 (1 H, brs).

1402

7-aza-N-(3-phenyl-5-isoxazolyl)-1-methylsulfonylspiro [indoline-3,4'-piperidine]-1'-carboxamide m.p.: 211–212° C.

EXAMPLE 15

1-Methylsufonyl-N-(4-ethoxycarbonylphenyl)spiro [indoline-3,4'-piperidine]-1'-carboxamide 1500

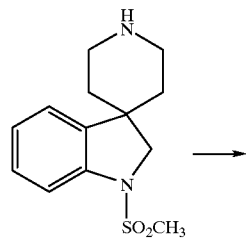

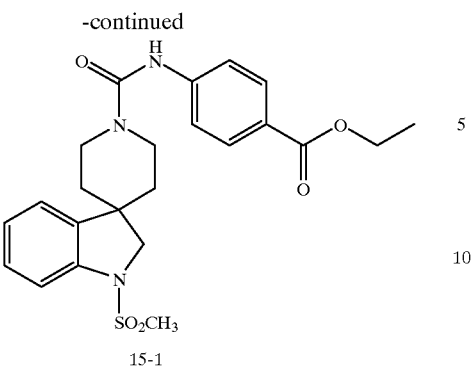

15-1

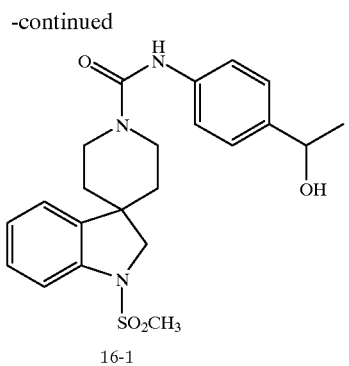

16-1

To a stirred solution of 1-methylsulfonyl-spiro[indoline-3,4'-piperidine] (2.66 g, 10 mmol) in dichloromethane (50 mL), was added ethyl 4-isocyanatobenzoate (1.91 g, 10 mmol) at room temperature. The resulting solution was stirred for four hours during which time precipitation occurred. The mixture was evaporated to remove dichloromethane, and then was suspended in methanol (20 mL), filtration followed by washing with cold methanol gave 1500 as a white solid (4.56 g, 100%)

NMR (CDCl3, 300 MHz): δ ppm 8.00 (d, J=8.8 Hz, 2 H); 7.46 (d, J=8.8 Hz, 2 H); 7.43–7.06 (m, 4 H); 6.62 (s, 1 H), 4.36 (q, J=7 Hz, 2 H), 4.14 (br. D,J=13 Hz, 2 H); 3.90 (s, 2 H), 3.09 (dt, J=1, 13 Hz, 2 H); 2.94 (s, 3 H), 2.00 (dt, J=4, 13 Hz, 2 H), 1.82 (br. d, J=13 Hz, 2 H), 1,38 (t, J=7 Hz, 3 H).

ESI-MS: 458 (M+1)

The following compounds were similarly prepared from 1-methylsulfonyl-spiro[indoline-3,4'-piperidine] and the appropriate isocyanates.

1501
1-methylsufonyl-N-(4-nitrophenyl)spiro[indoline-3,4'-pipenridine]-1'-carboxamide, ESI-MS: 431 (M+1);

1502
1-methylsufonyl-N-(4-acetylphenyl)spiro[indoline-3,4'-piperidine]-1'-carboxamide, ESI-MS: 428 (M+1);

1503
1-methylsufonyl-N-(4-methylthiophenyl)spiro[indoline-3,4'-piperidine]-1'-carboxamide, ESI-MS: 431 (M+1);

1504
1-methylsufonyl-N-(3,4-dichlorophenyl)spiro[indoline-3,4'-piperidine]-1'-carboxamide, ESI-MS: 454 (M+1);

1505
1-methylsufonyl-N-(4-phenylphenyl)spiro[indoline-3,4'-piperidine]-1'-carboxamide, ESI-MS: 462 (M+1);

EXAMPLE 16

1-Methylsufonyl-N-(4-(2-hydroxyethyl)phenyl)spiro[indoline-3,4'-piperidine]-1'-carboxamide 1600

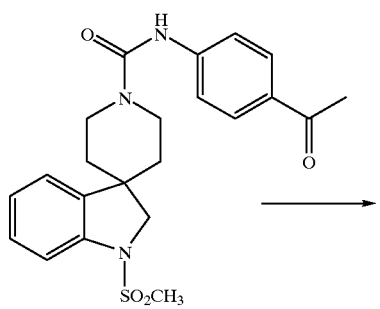

To a stirred solution of 1-methylsufonyl-N-(4-acetylphenyl)spiro[indoline-3,4'-piperidine]-1'-carboxamide (400 mg) in ethanol/dichloromethane (5/5 mL) at 0° C., was added sodium borohydride (100 mg). The mixture was stirred for 1 hour, then 3 N HCl (0.2 mL) was added to destroy the excess hydride. The mixture was then concentrated and partitioned between water and dichloromethane. The organic layer was dried over MgSO4 and evaporated to give the title compound, 1600 as white powder (386 mg). ESI-MS: 430 (M+1)

EXAMPLE 17

1-Sulfamoyl-N-(3,4-dichlorophenyl)spiro[indoline-3,4'-piperidine]-1'-carboxamide 1700

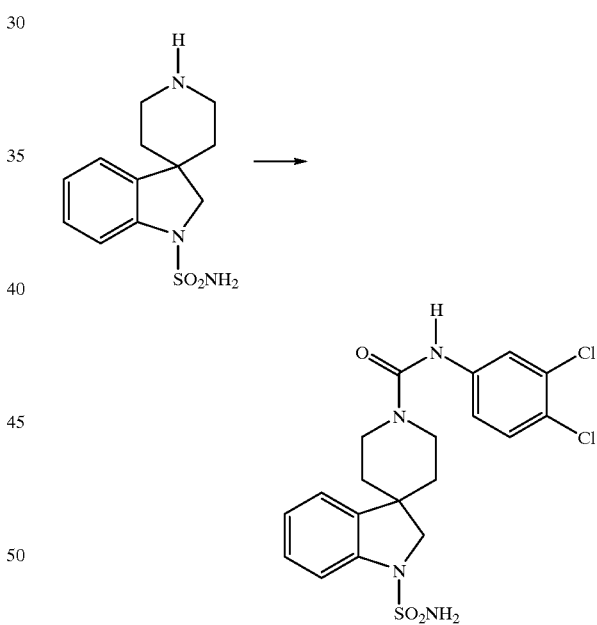

1700

This compound was prepared from 1-sulfamoylspiro[indoline-3,4'-piperidine] (L. Guo, A. Patchett, L. Yang, U.S. Pat. No. 5,783,582, Jul. 21, 1998.) and 3,4-dichlorophenyl isocyanate by the same procedures described in Example 15

NMR (DMSO-d6, 400 MHz): δ ppm: 8.84 (s, 1 H), 7.87 (s, 1 H), 7.47 (s, 2 H), 7.31–7.25 (m, 4 H), 7.18 (t, J=7.6 Hz, 1 H), 6.98 (t, J=7.6 Hz, 1 H), 4.13 (d, J=13.6 Hz, 2 H), 3.81 (s, 2 H), 3.02–2.94 (m, 2 H), 1.79–1.74 (m, 2 H), 1.65 (d, J=13.2 Hz, 2 H) ESI-MS: 455 (M+1)

Employing substantially the same procedure as described in Example 15, the following compounds were prepared from 1-sulfamoyl-spiro[indoline-3,4'-piperidine] and the appropriate isocyanate.

1701
1-Sulfamoyl-N-(4-ethoxycarbonylphenyl)spiro[indoline-3,4'-piperidine]-1'-carboxamide, ESI-MS: 459 (M+1);

1702
1-Sulfamoyl-N-(4-chlorophenyl)spiro[indoline-3,4'-piperidine]-1'-carboxamide, ESI-MS: 421 (M+1)

1703
1-Sulfamoyl-N-(3,4-dimethylphenyl)spiro[indoline-3,4'-piperidine]-1'-carboxamide, ESI-MS: 415 (M+1);

1704
1-Sulfamoyl-N-(2,4-dimethoxyphenyl)spiro[indoline-3,4'-piperidine]-1'-carboxamide, ESI-MS: 447 (M+1);

1705
1-Sulfamoyl-N-(2,6-dichlorophenyl)spiro[indoline-3,4'-piperidine]-1'-carboxamide, ESI-MS: 455 (M+1);

1706
1-Sulfamoyl-N-(3-chlorophenyl)spiro[indoline-3,4'-piperidine]-1'-carboxamide, ESI-MS: 421 (M+1)

1707
1-Sulfamoyl-N-(4-nitrophenyl)spiro[indoline-3,4'-piperidine]-1'-carboxamide, ESI-MS: 432 (M+1);

1708
1-Sulfamoyl-N-(2-chlorophenyl)spiro[indoline-3,4'-piperidine]-1'-carboxamide, ESI-MS: 421 (M+1);

1709
1-Sulfamoyl-N-(3-nitrophenyl)spiro[indoline-3,4'-piperidine]-1'-carboxamide, ESI-MS: 432 (M+1);

1710
1-Sulfamoyl-N-(2-nitrophenyl)spiro [indoline-3,4'-piperidine]-1'-carboxamide, ESI-MS: 432 (M+1);

1711
1-Sulfamoyl-N-(4-ethoxyphenyl)spiro[indoline-3,4'-piperidine]-1'-carboxamide, ESI-MS: 431 (M+1);

1712
1-Sulfamoyl-N-(2-methoxyphenyl)spiro[indoline-3,4'-piperidine]-1'-carboxamide, ESI-MS: 431 (M+1);

1713
1-Sulfamoyl-N-(4-phenyloxyphenyl)spiro[indoline-3,4'-piperidine]-1'-carboxamide, ESI-MS: 479 (M+1);

1714
1-Sulfamoyl-N-(4-methoxyphenyl)spiro[indoline-3,4'-piperidine]-1'-carboxamide, ESI-MS: 417 (M+1);

1715
1-Sulfamoyl-N-(3-methoxyphenyl)spiro[indoline-3,4'-piperidine]-1'-carboxamide, ESI-MS: 431 (M+1);

1716
1-Sulfamoyl-N-(3-ethoxyphenyl)spiro[indoline-3,4'-piperidine]-1'-carboxamide, ESI-MS: 431 (M+1);

1717
1-Sulfamoyl-N-(4-isopropylphenyl)spiro[indoline-3,4'-piperidine]-1'-carboxamide, ESI-MS: 429 (M+1);

1718
1-Sulfamoyl-N-(2-ethylphenyl)spiro[indoline-3,4'-piperidine]-1'-carboxamide, ESI-MS: 415 (M+1);

1719
1-Sulfamoyl-N-(4-methylphenyl)spiro [indoline-3,4'-piperidine]-1'-carboxamide, ESI-MS: 401 (M+1);

1720
1-Sulfamoyl-N-(3-methylphenyl)spiro[indoline-3,4'-piperidine]-1'-carboxamide, ESI-MS: 401 (M+1);

1721
1-Sulfamoyl-N-phenyl-spiro[indoline-3,4'-piperidine]-1'-carboxamide, ESI-MS: 401 (M+1);

1722
1-Sulfamoyl-N-(4-acetylphenyl)spiro[indoline-3,4'-piperidine]-1'-carboxamide ESI-MS: 429 (M+1);

EXAMPLE 18
trans-N-(5-acetyl-2-pyrimidinyl)-1-methylsulfonylspiro[indoline-3,4'-cyclohexane]-1'-carboxamide (#1800)

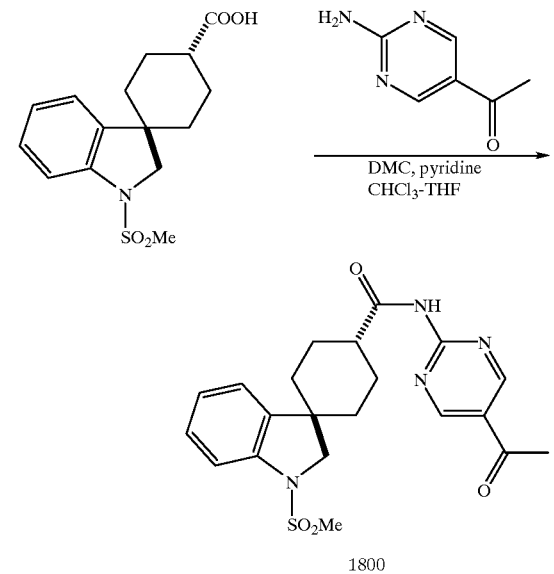

Pyridine (0.121 mL, 1.50 mmol) and trans-1-methylsulfonylspiro[indoline-3,4'-cyclohexane]-1'-carboxylic acid [prepared by the method of Example 9] (92.8 mg, 0.330 mmol) were added to a solution of 2-chloro-1,3-dimethylimidazolium chloride (152 mg, 0.90 mmol) in CHCl$_3$ (0.800 mL) and THF (0.800 mL). After stirring for 5 min at room temperature, 2-amimo-5-acetylpyrimidine was added to the mixture. The resulting mixture was stirred at room temperature for 2.5 h. The mixture was diluted with EtOAc, washed with 5% KHSO$_4$, sat. NaHCO$_3$ and brine, dried (MgSO$_4$). After removal of the solvent, the residue was purified by column chromatography on silica gel (CHCl$_3$/MeOH=100/0→99/1) to give an oil, which was triturated with EtOAc-hexane to give 1800 (93.8 mg, 56%) as a white powder.

m.p.: 100–105° C.

Compounds #1801–1803 were prepared from 2-amino-5-acetylpyrazine in analogy to the procedure of Example 10.

1801 trans-N-(5-acetyl-2-pyrazinyl)-1-methylsulfonylspiro[indoline-3,4'-cyclohexane]-1'-carboxamide m.p.: 220.8–221.2° C.

The following compounds #1802–#1803 were prepared from 6-fluoro-1-methylsulfonylspiro[indoline-3,4'-cyclohexane]-1'-carboxylic acid [prepared by the method of Example 9] and the appropriate amines in analogy to the procedure of Example 10.

1802
trans-N-(5-acetyl-2-pyrimidinyl)-6-fluoro-1-methylsulfonylspiro[indoline-3,4'-cyclohexane]-1'-carboxamide m.p.: 196–198° C.

1803
trans-N-(5-acetyl-2-pyrazinyl)-6-fluoro-1-methylsulfonylspiro[indoline-3,4'-cyclohexane]-1'-carboxamide m.p.: 228.1–228.3° C.

The following compounds #1804–#1805 were prepared from 5-fluoro-1-methylsulfonylspiro[indoline-3,4'-cyclohexane]-1'-carboxylic acid [prepared by the method of Example 9] and the appropriate amines in analogy to the procedure of Example 10.

1804
trans-N-(5-acetyl-2-pyrimidinyl)-5-fluoro-1-methylsulfonylspiro[indoline-3,4'-cyclohexane]-1'-carboxamide
m.p.: 210.5–211.7° C.

1805
trans-N-(5-acetyl-2-pyrazinyl)-5-fluoro-1-methylsulfonylspiro[indoline-3,4'-cyclohexane]-1'-carboxamide
m.p.: 209.3–209.6° C.

EXAMPLE 19

Determination of $IC_{50}$

LMtk- cells expressing human Y5 receptors were washed with 50 mM HEPES buffer (pH 7.4) containing 20% sucrose, homogenized and centrifuged at 1,000×g for 15 min. The supernatant was centrifuged at 100,000×g for 45 min. The pellets were resuspended in 5 mM HEPES buffer (pH 7.4) and centrifuged again. The membrane fraction was resuspended by a homogenizer in the same buffer and used for this study. Binding of $[^{125}I]$PYY to the membrane was performed in 0.2 ml of 25 mM Tris buffer (pH 7.4) containing 10 mM $MgCl_2$, 1 mM PMSF, 0.1% bacitracin and 0.5% BSA. The membranes (100–300 μg/ml) were incubated at 25° C. for 120 min with $[^{125}I]$PYY (25 pM). Bound and free peptides were separated by filtration using a GF/C glass filter (Whatman, England) presoaked with 0.3% polyethylenimine. The remaining radioactivity on the filter was quantitated using a Cobra™ (Packard, Japan). Specific binding of $[^{125}I]$PYY was defined as the difference between total binding and nonspecific binding in the presence of 1 μM PYY.

Employing the procedure described in Example 18, a representative number of the compounds of this invention were found to have IC50 values less than 1 mM.

Using procedures similar to those described in Example 18, in which membranes expressing other NPY subtypes are used in place of the Y5 membranes, many of the compounds of this invention have great selectivity for the Y5 receptor over the NPY Y1, Y2 and Y4 receptors. For example, many of the compounds of this invention have IC50>1000 nM on Y1, Y2 and Y4 receptors.

EXAMPLE 20

Effect of Compound 100 on bovine pancreatic polypeptide (bPP)-induced food intake in Sprague-Dawley rats.

Materials and Methods

Male Sprague-Dawley rats aged 7 weeks (Charles River, Japan) were maintained under the controlled temperature (23±3° C.), humidity (55±15%) and light-dark cycle (7:00–19:00 light on). Rats were housed individually with ad libitum access food (CE-2, Clea Japan) and tap water.

Rats were anesthetized with sodium pentobarbital (50 mg/kg, i.p., Dainabot, Japan). A permanent stainless steel guide cannula for intracerebroventricular (ICV) injection (21 gauge, 10 mm long) was stereotaxically implanted into the right lateral ventricle. The stereotaxic coordinates used were as follows: 0.9 mm posterior and 1.2 mm lateral to the bregma and 1.5 mm ventral to the brain surface.

Animals were allowed at least 6-day recovery postoperatively before the start of feeding experiment. The day before the experiment, they were handled and underwent mock injection, and nocturnal food intake was measured. Rats which ate more than 15 g during the night before the experiment were used for the following experiment.

Test compounds were suspended in 0.5% methylcellulose and orally administered by gavage. Administration of test compounds usually began at 10:00. Dosing volume was 5 ml/kg. One hour after the drug administration, bovine pancreatic polypeptide (PP, 5 g/10 1/1 min) was ICV injected through a stainless steel injector (26 gauge) attached to a 50 1 Hamilton microsyringe by polyethylene tubing. The injector extended 2 mm beyond the end of the guide cannula. Bovine PP was dissolved in 10 mM PBS containing 0.05% BSA. Two hour post-injection food intake was measured for each rat.

Results

Compound 100 was orally administered 1 hour prior to the ICV-injection of bPP in satiated male Sprague-Dawley rats. Compound 100 (1, 3, 10 and 30 mg/kg) suppressed bPP-induced food intake in a dose-dependent manner, and the minimum effective dose is estimated to be 3 mg/kg. Furthermore, this compound at 100 mg/kg, p.o. did not cause any abnormal behavior in rats and mice during 24 hour after dosing. Thus, Compound 100 has a potent in vivo Y5 antagonistic activity without causing any abnormal behavior.

EXAMPLE 21A

Tablets containing 1–25 mg of compound

|  | Amount mg | | |
| --- | --- | --- | --- |
| Compound of formula I | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium stearate | 0.5 | 0.5 | 0.5 |

EXAMPLE 21B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium stearate | 0.5 | 0.5 | 0.5 |

What is claimed is:

1. A compound of structural formula I:

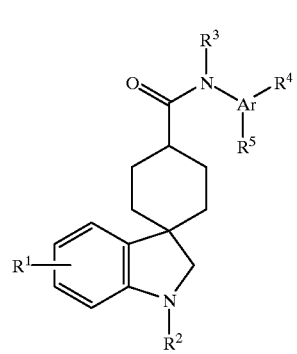

or a pharmaceutically acceptable salt thereof, wherein;
$R^1$ is H, $C_{1-3}$ alkyl, $C_{1-3}$ alkoxy, F, or Cl;
$R^2$ is $S(O)_nR^6$, $COR^6$ or CHO, wherein
n is 0, 1 or 2; and $R^6$ is $N(R^3)_2$ or $C_{1-3}$ alkyl;

$R^3$ is independently H or $C_{1-3}$ alkyl;

Ar is aryl ot heteroaryl;

$R^4$ and $R^5$ are independently selected from:
(1) hydrogen,
(2) aryl, either unsubstituted or substituted with
    (a) halo
    (b) $C_{1-3}$ alkoxy,
    (c) —N($C_{1-3}$ alkoxy)$_2$,
    (d) $C_{2-4}$ alkanoyl, or
    (e) aryl;
(3) nitro,
(4) $C_{1-5}$ alkyl,
(5) $C_{1-5}$ alkoxy,
(6) hydroxy-$C_{1-3}$ alkyl,
(7) carboxy,
(8) halo,
(9) $C_{1-5}$ alkylthio,
(10) $C_{1-5}$ alkoxycarbonyl,
(11) pyridylcarbonyl,
(12) benzoyl,
(13) phenyl-$C_{1-3}$ alkoxy,
(14) pyridyl, either unsubstituted or substituted with $C_{1-3}$ alkyl or $C_{1-3}$ alkoxy,
(15) $C_{3-6}$ cycloalkyl,
(16) oxazolyl,
(17) thiazolyl,
(18) triazolyl,
(19) phenoxy or
(20) $C_{2-6}$ alkanoyl.

2. The compound of claim 1 wherein Ar is phenyl, of structural formula I(a)

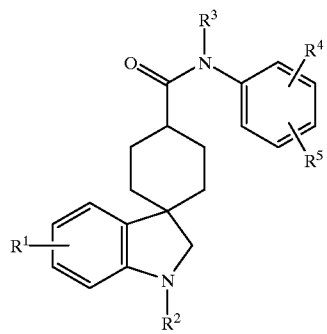

I(a)

or a pharmaceutically acceptable salt thereof.

3. The compound of claim 2 wherein $R^2$ is —$SO_2(C_{1-3}$ alkyl) or $SO_2NH_2$.

4. The compound of claim 3 wherein $R^4$ and $R^5$ are independently selected from: phenyl, pyridyl, benzoyl, halophenyl, phenoxy, $C_{1-5}$ alkylpyridyl, benzhydryl, phenyl-$C_{1-3}$ alkoxy, $NO_2$, $C_{2-4}$ alkanoyl, halo, $C_{1-5}$ alkoxy, $C_{1-3}$ alkoxycarbonyl, $C_{1-5}$ alkylthio, triazolyl, carboxy, hydrogen, $C_{1-5}$ alkyl, pyridylcarbonyl, and $C_{1-3}$ alkoxyphenyl.

5. The compound of claim 4 or a pharmaceutically acceptable salt thereof selected from those depicted in the following Table:

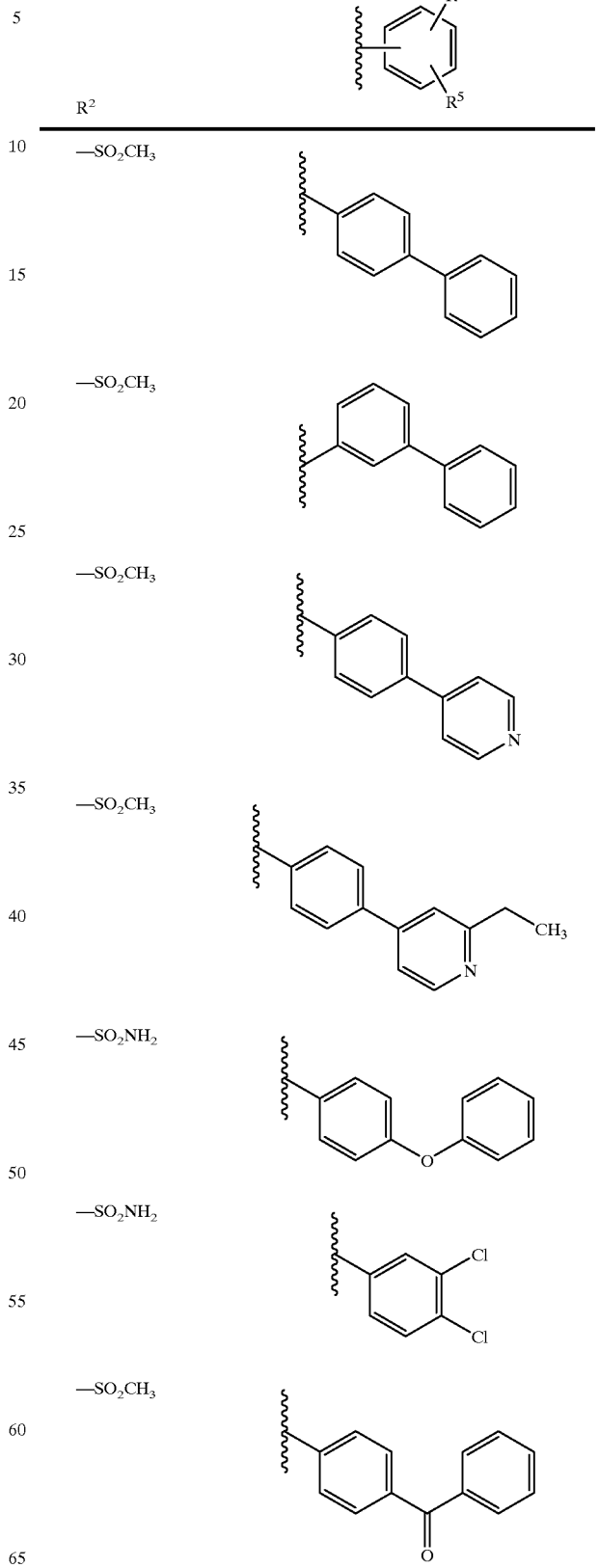

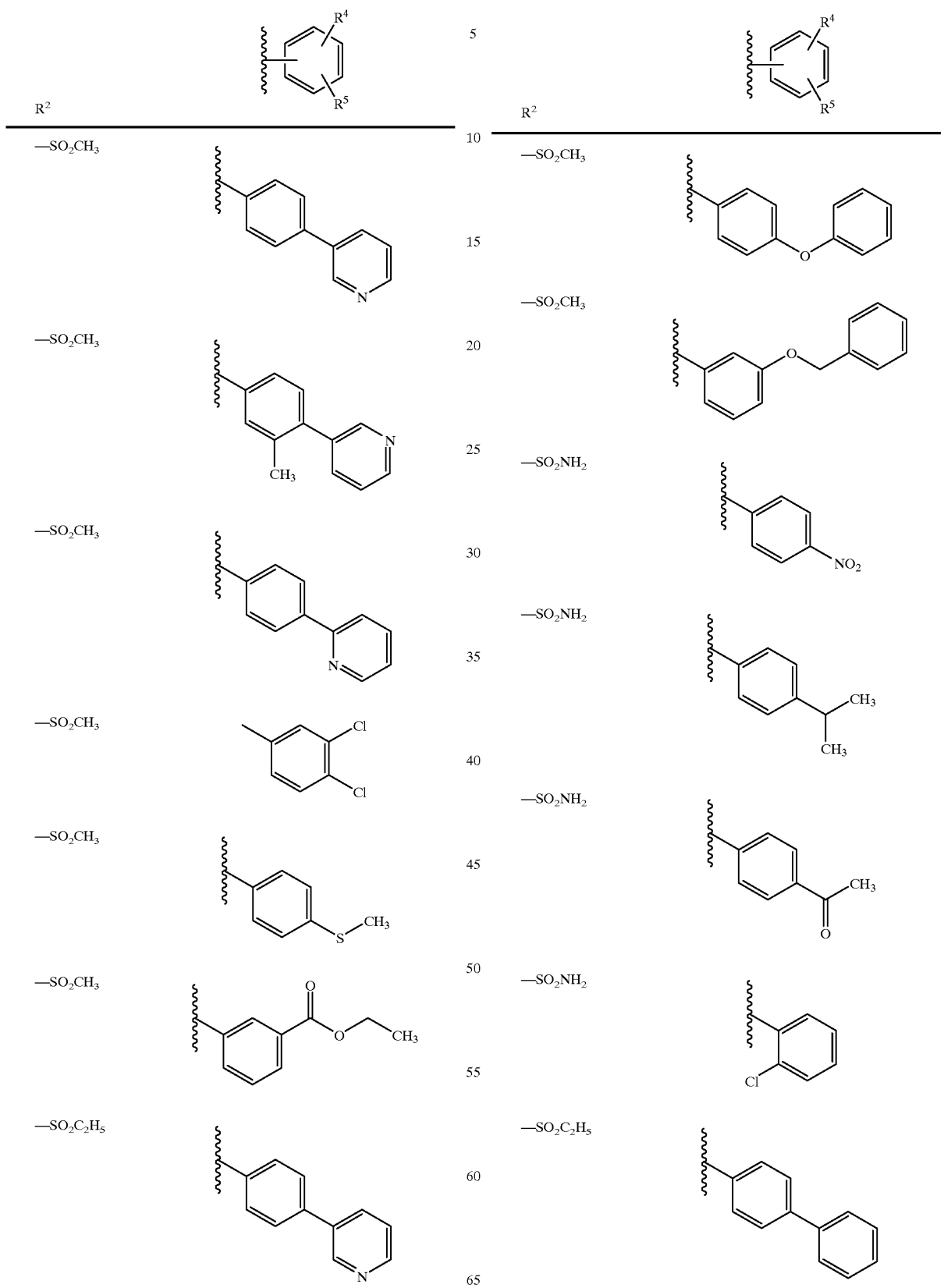

| $R^2$ | |
|---|---|
| —SO$_2$CH(CH$_3$)$_2$ | 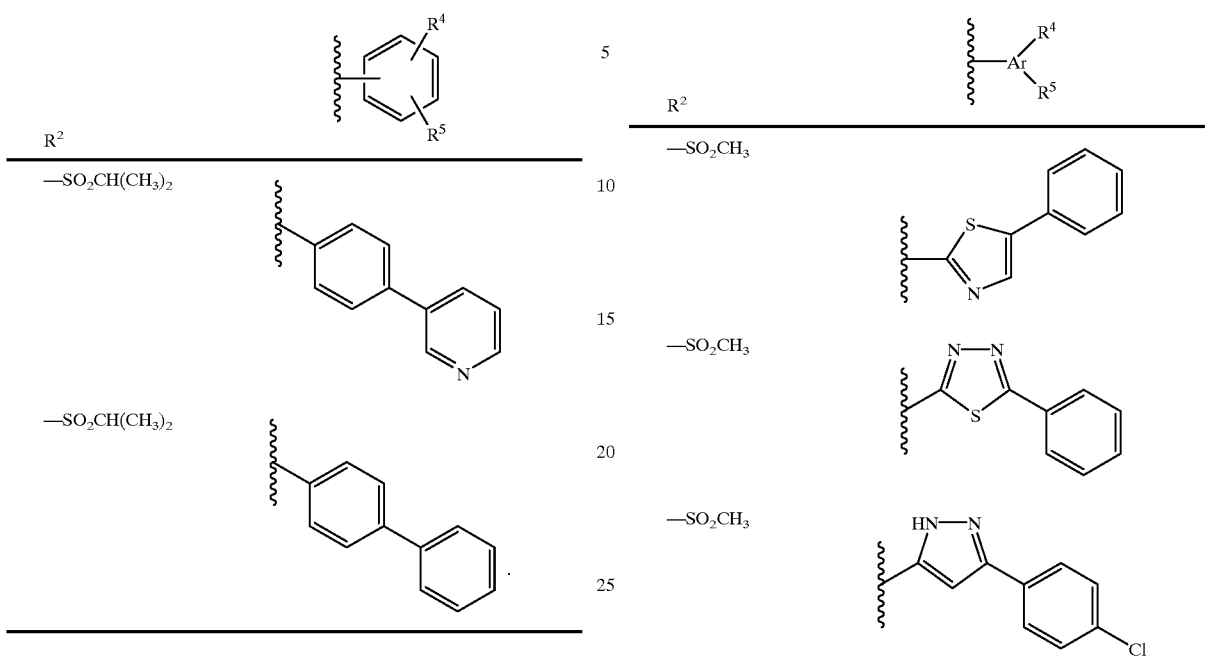 |
| —SO$_2$CH(CH$_3$)$_2$ | |

6. The compound of claim 1 wherein Ar is a 5- or 6-membered heteroaryl having, besides carbon atoms, 1 to 3 heteroatoms selected from N, O or S as atoms constituting the ring, or benzo- or pyrido-fused versions therof of structural formula I(b);

I(b)

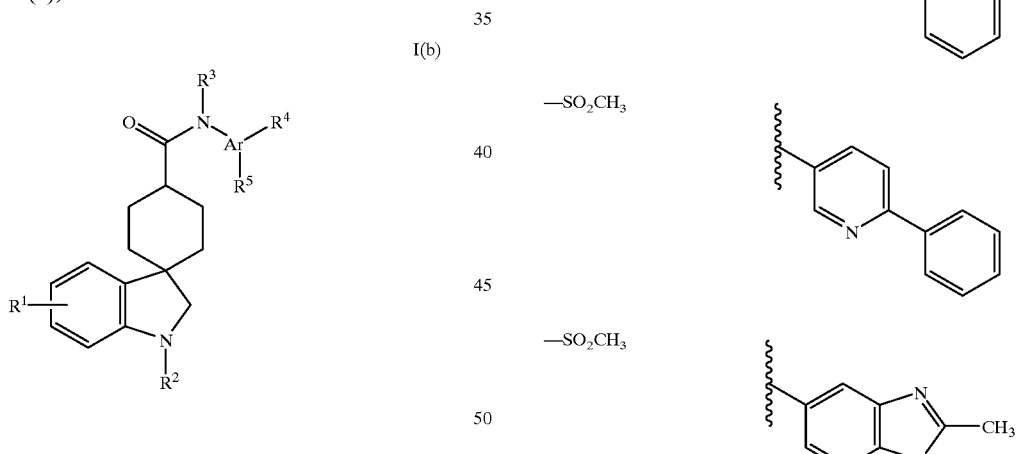

or a pharmaceutically acceptable salt thereof.

7. The compound of claim 6 wherein R$^2$ is —SO$_2$(C$_{1-3}$ alkyl) or —SO$_2$N(C$_{1-3}$ alkyl)$_2$.

8. The compound of claim 7 wherein the heteroaryl group, Ar, is selected from: thiazolyl, thiadiazolyl, pyrazolyl, pyridyl, benzothiazolyl, oxazolyl, pyridothiazolyl, benzoxazolyl, quinolyl, pyrazinyl, thienyl, isoxazolyl, pyrimidinyl, benzimidazolyl, oxadiazolyl and imidazolyl.

9. The compound of claim 8, or a pharmaceutically acceptable salt thereof, selected from those depicted in the following Table:

| $R^2$ | |
|---|---|
| —SO$_2$CH$_3$ | 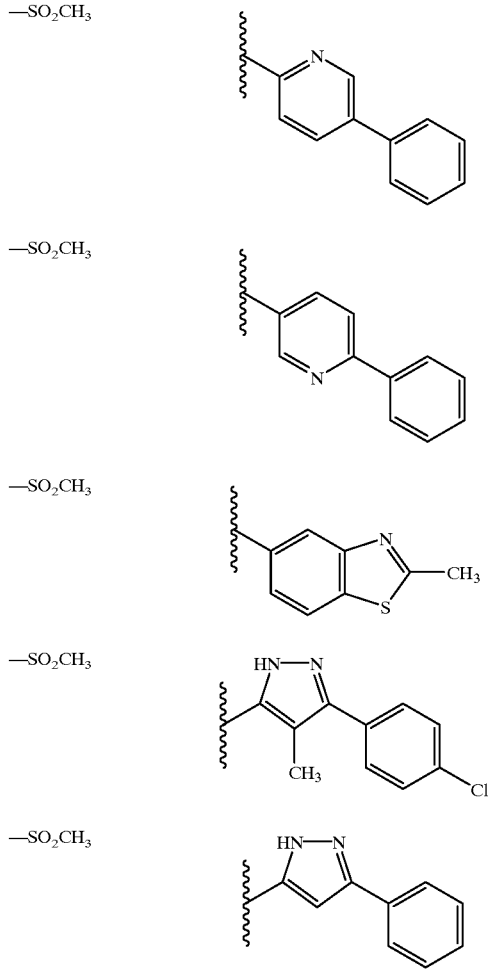 |
| —SO$_2$CH$_3$ | |
| —SO$_2$CH$_3$ | |
| —SO$_2$CH$_3$ | |
| —SO$_2$CH$_3$ | |
| —SO$_2$CH$_3$ | |
| —SO$_2$CH$_3$ | |
| —SO$_2$CH$_3$ | |

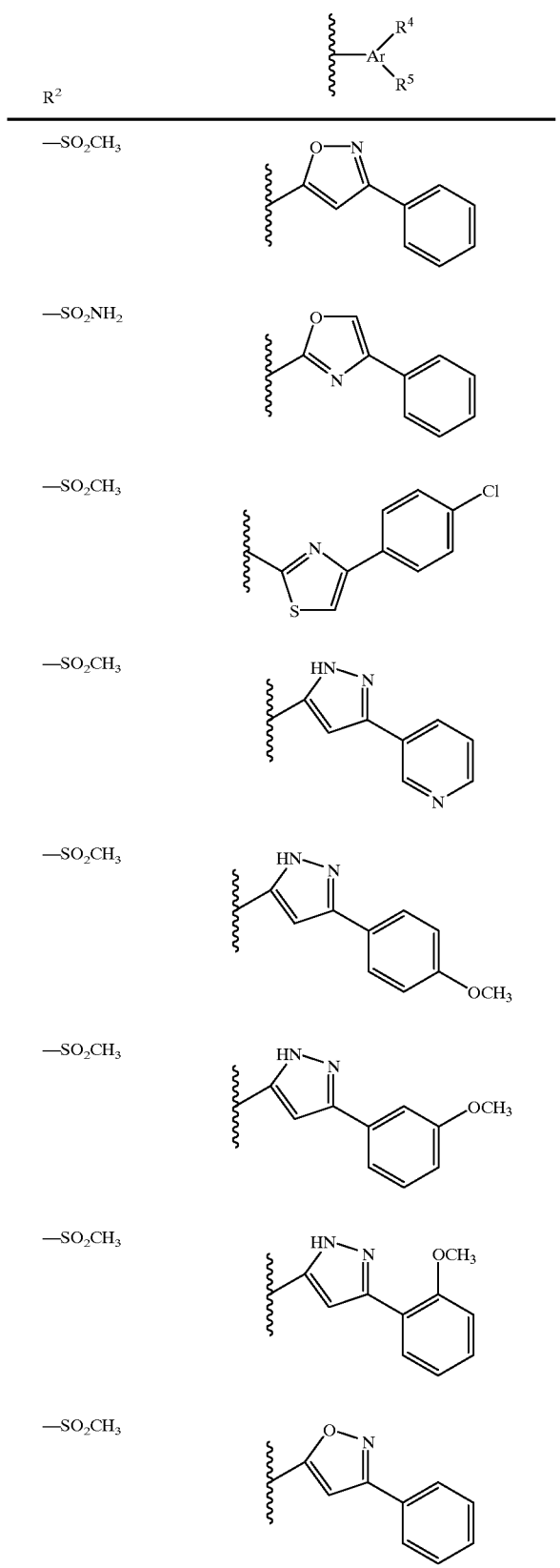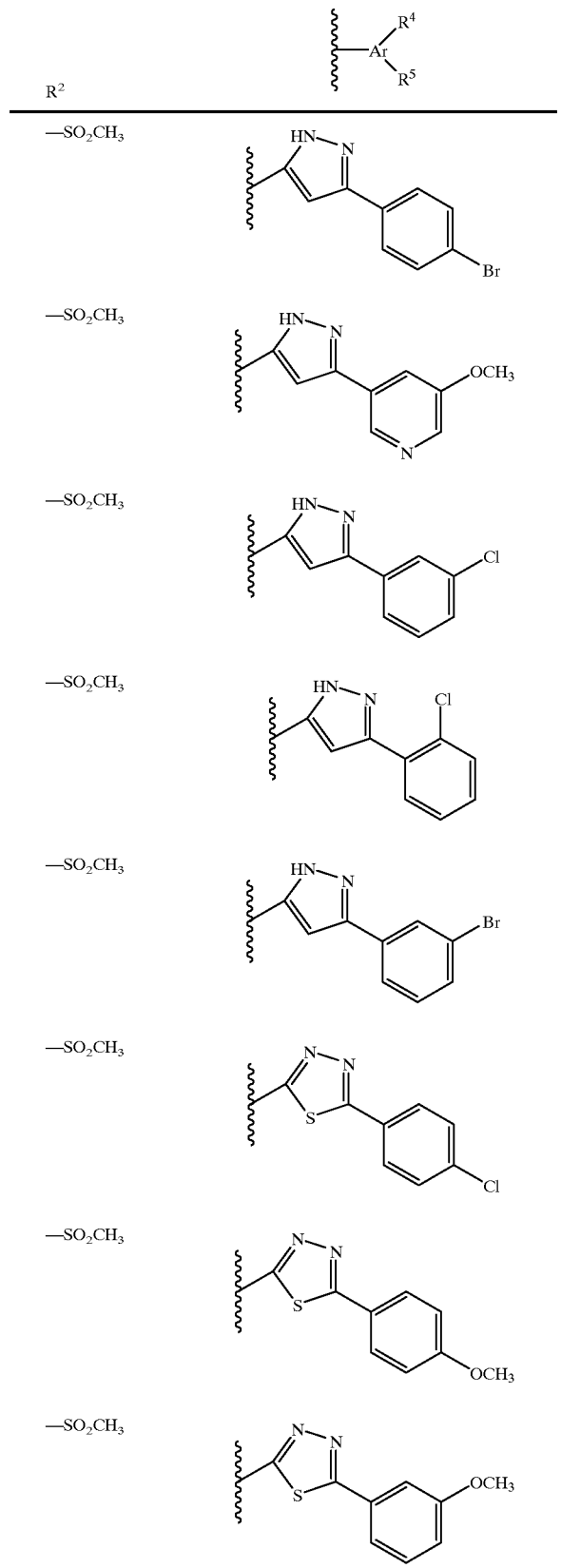

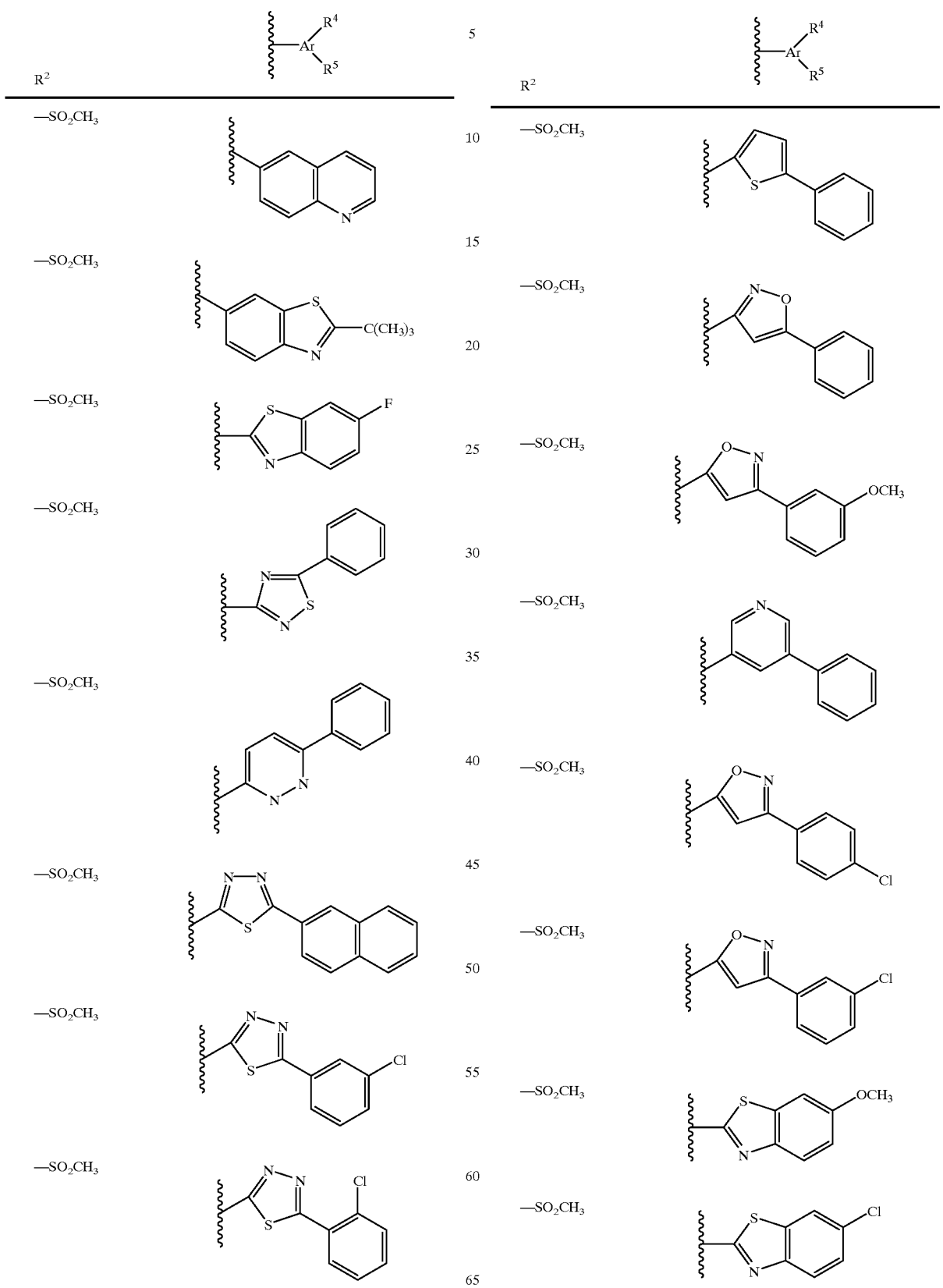
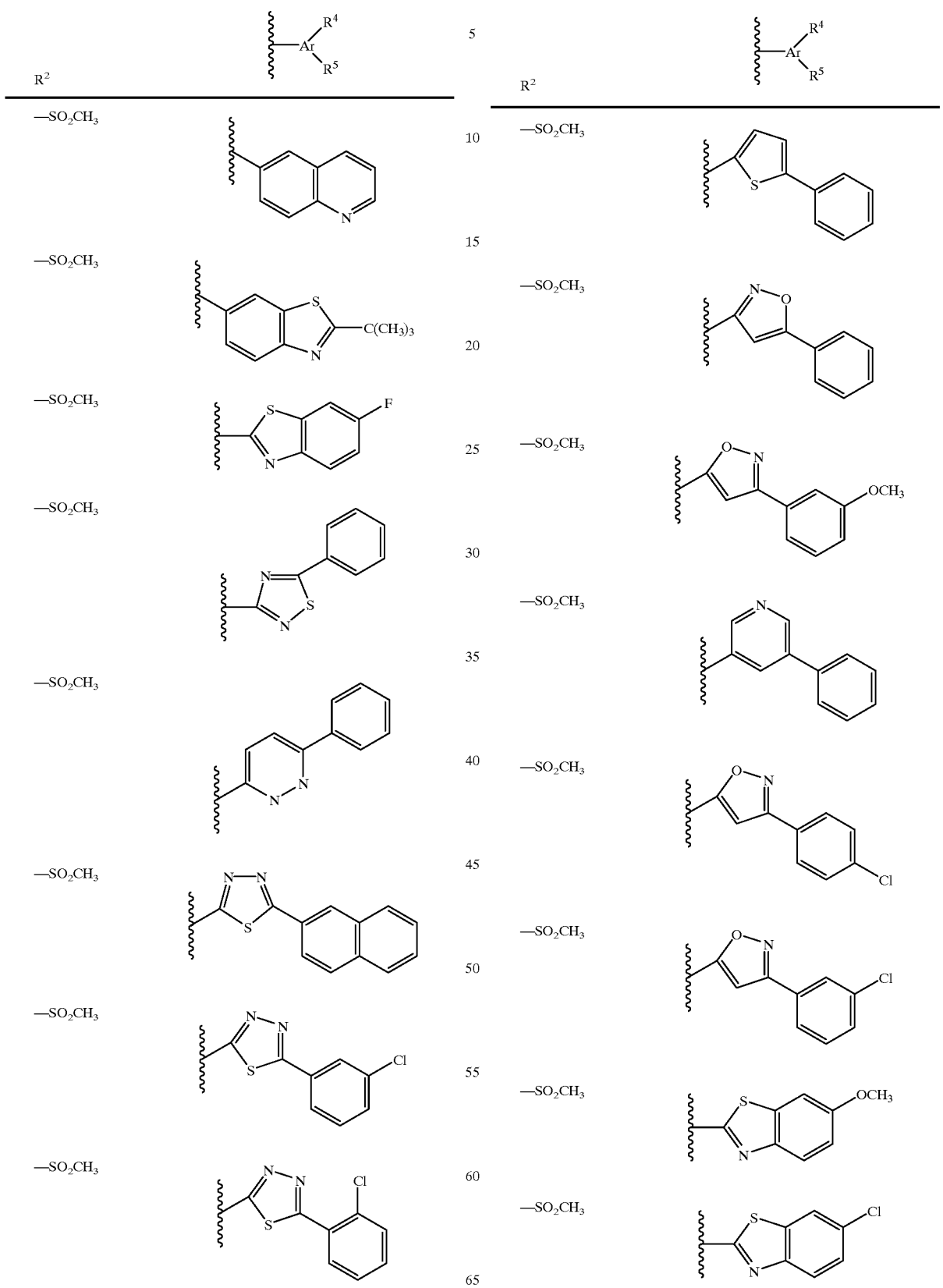

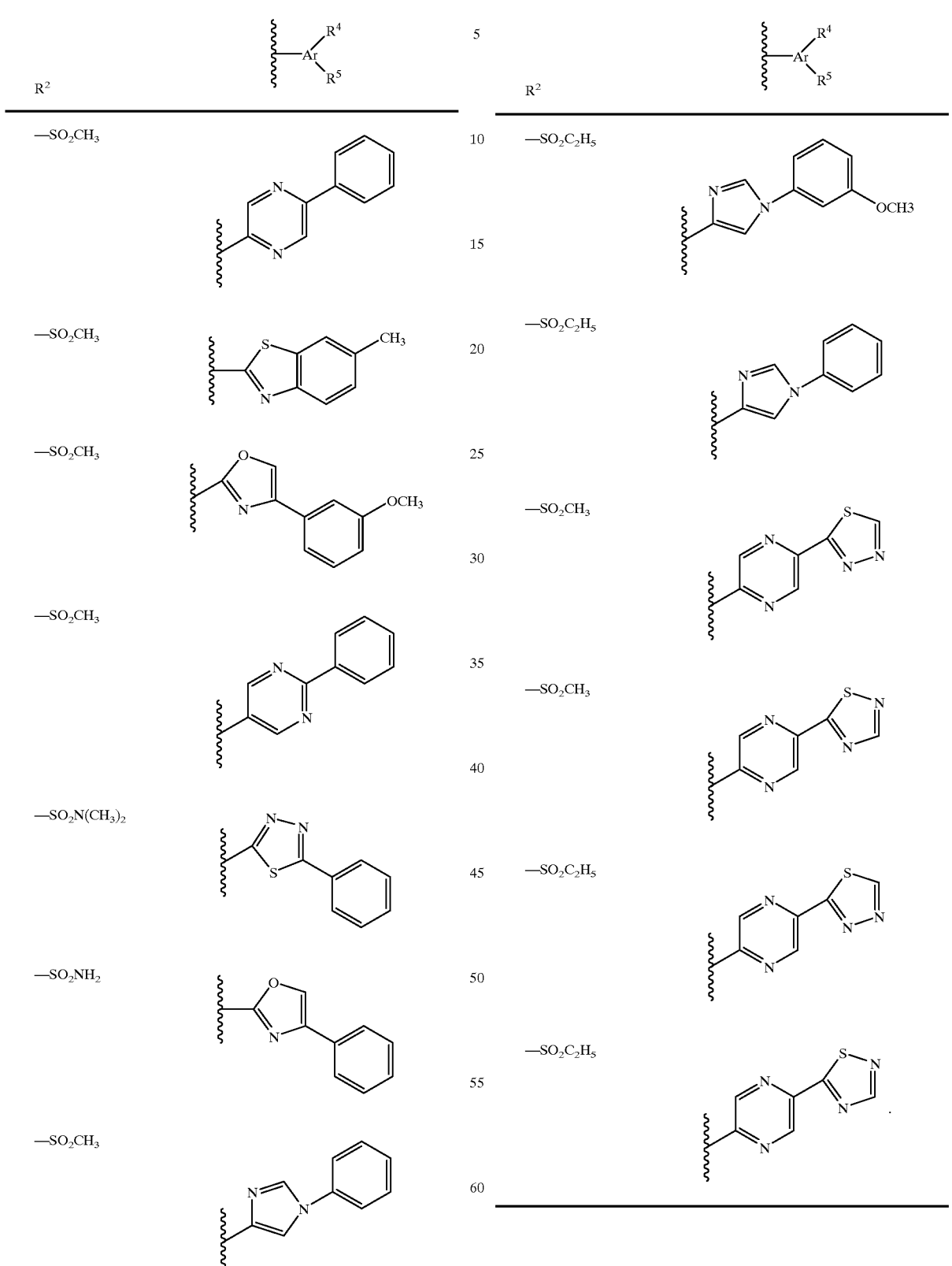
10. The compound of claim 1 or a pharmaceutically acceptable salt thereof, selected from those depicted in the following Table;

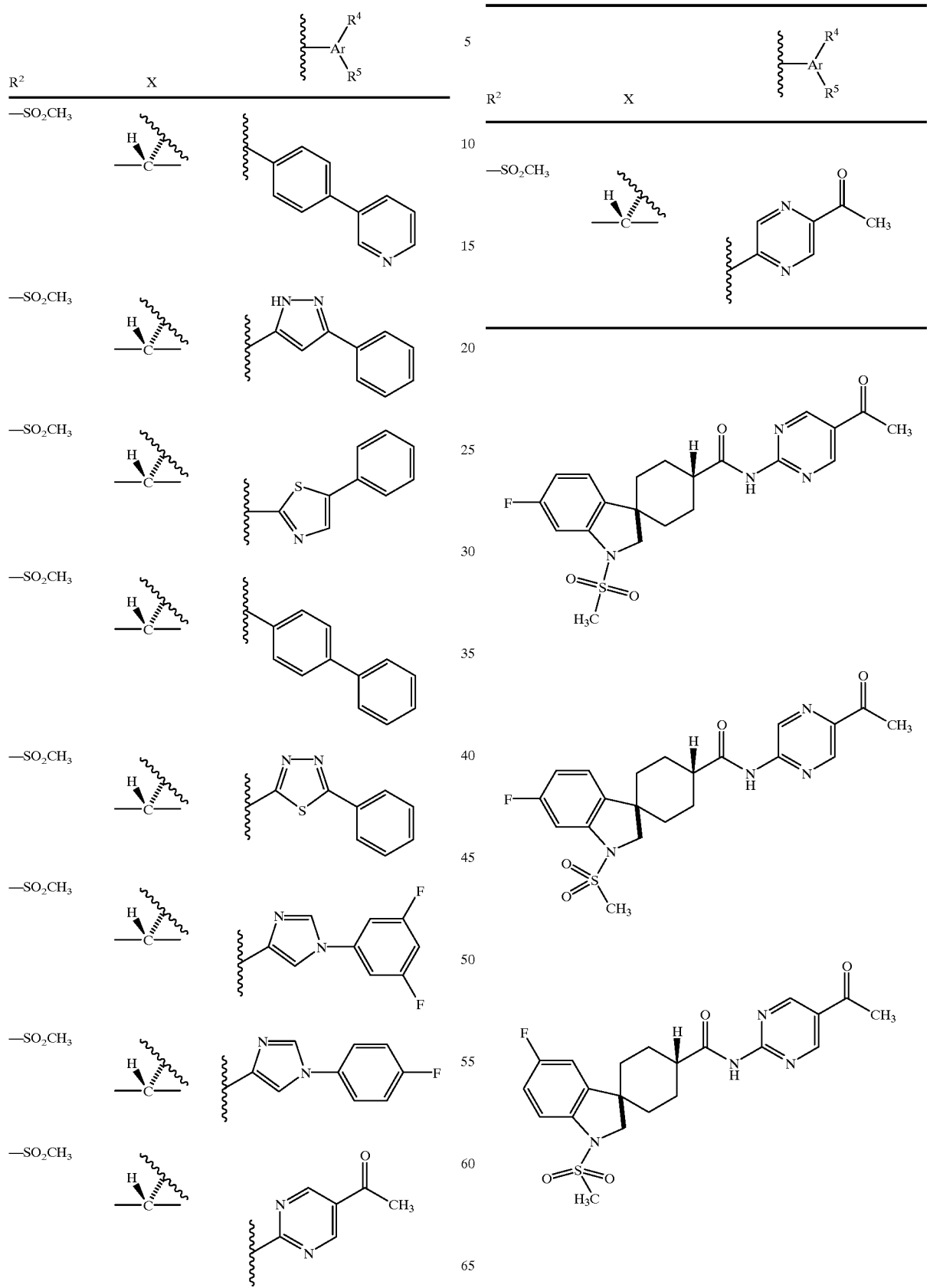

-continued

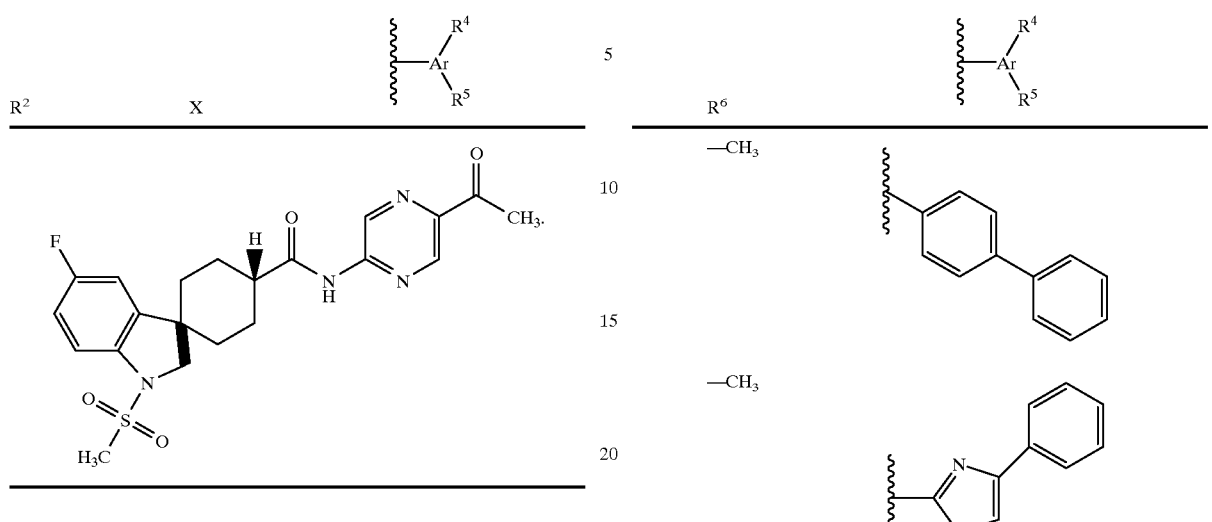

11. The compound of claim 1 wherein $R^2$ is $-COR^6$ of structural formula I(d):

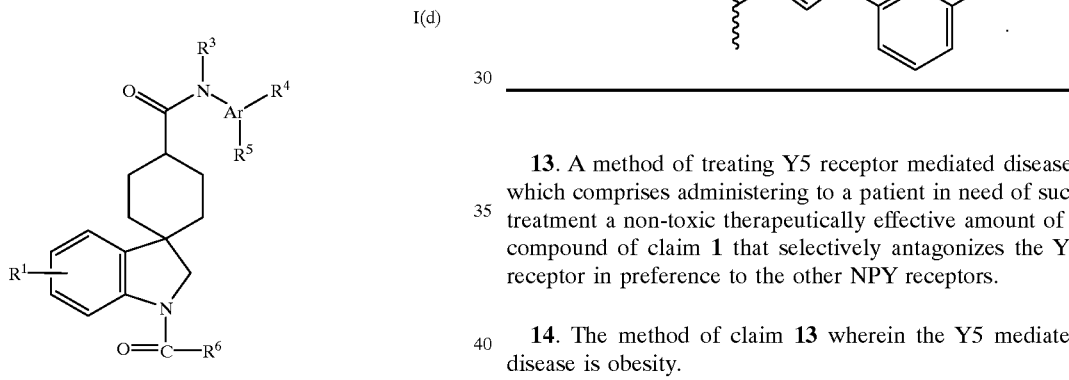

I(d)

or a pharmaceutically acceptable salt thereof.

12. The compound of claim 11 or a pharmaceutically acceptable salt thereof selected from those depicted in the following Table:

13. A method of treating Y5 receptor mediated diseases which comprises administering to a patient in need of such treatment a non-toxic therapeutically effective amount of a compound of claim 1 that selectively antagonizes the Y5 receptor in preference to the other NPY receptors.

14. The method of claim 13 wherein the Y5 mediated disease is obesity.

15. A pharmaceutical composition which comprises a pharmaceutically acceptable carrier and an effective amount of a compound of claim 1 that selectively antagonizes the Y5 receptor.

* * * * *